US006046152A

United States Patent [19]
Vinson et al.

[11] Patent Number: 6,046,152
[45] Date of Patent: Apr. 4, 2000

[54] LIQUID CLEANING COMPOSITIONS CONTAINING SELECTED MID-CHAIN BRANCHED SURFACTANTS

[75] Inventors: Phillip Kyle Vinson, Fairfield; Peter Robert Foley, Cincinnati; Thomas Anthony Cripe, Loveland; Daniel Stedman Connor, Cincinnati, all of Ohio

[73] Assignee: The Procter & Gamble Company, Cincinnati, Ohio

[21] Appl. No.: 09/170,425

[22] Filed: Oct. 13, 1998

Related U.S. Application Data

[63] Continuation of application No. PCT/US97/06473, Apr. 16, 1997
[60] Provisional application No. 60/015,521, Apr. 16, 1996, provisional application No. 60/015,523, Apr. 16, 1996, and provisional application No. 60/031,762, Nov. 26, 1996.

[51] Int. Cl.$^7$ .............................. C11D 1/29; C11D 3/43
[52] U.S. Cl. .................. 510/428; 510/119; 510/122; 510/125; 510/426; 510/427; 510/506
[58] Field of Search ................................ 568/454, 882; 560/76; 510/506, 226, 321, 325, 304, 119, 122, 125, 426, 428, 427

[56] References Cited

U.S. PATENT DOCUMENTS

| | | | |
|---|---|---|---|
| 2,695,327 | 11/1954 | Ziegler et al. | 260/683.15 |
| 2,934,568 | 4/1960 | Baker et al. | 260/615 |
| 3,480,556 | 11/1969 | DeWitt et al. | 252/152 |
| 3,647,906 | 3/1972 | Farley | 260/683 |
| 3,775,349 | 11/1973 | Tuvell et al. | 252/547 |
| 3,887,624 | 6/1975 | Gibson et al. | 260/615 B |
| 4,075,129 | 2/1978 | Murata et al. | 252/527 |
| 4,102,823 | 7/1978 | Matheson | 252/533 |
| 4,111,855 | 9/1978 | Barrat et al. | 252/545 |
| 4,732,707 | 3/1988 | Naik et al. | 252/548 |
| 4,870,038 | 9/1989 | Page et al. | 502/62 |
| 5,026,933 | 6/1991 | Blain et al. | 585/7 |
| 5,030,774 | 7/1991 | Oswald et al. | 568/882 |
| 5,245,072 | 9/1993 | Giacobbe et al. | 560/99 |
| 5,284,989 | 2/1994 | Apelian et al. | 585/533 |
| 5,446,213 | 8/1995 | Sato et al. | 568/883 |
| 5,562,866 | 10/1996 | Hu et al. | 510/432 |
| 5,780,694 | 7/1998 | Singleton | 568/909 |

FOREIGN PATENT DOCUMENTS

| | | |
|---|---|---|
| 1086178 | 9/1980 | Canada .................. 134/3.11 |
| 0342917 | 11/1989 | European Pat. Off. . |
| 0401642 | 12/1990 | European Pat. Off. . |
| 0439316 | 7/1991 | European Pat. Off. . |
| 0684300 | 11/1995 | European Pat. Off. . |
| 1151630 | 2/1958 | France . |
| 2176794 | 11/1973 | France . |
| 2267369 | 7/1975 | France . |
| 2424316 | 11/1979 | France . |
| 2243307 | 9/1972 | Germany . |
| 719445 | 12/1954 | United Kingdom . |
| 1399966 | 7/1975 | United Kingdom . |
| WO 85/02175 | 5/1985 | WIPO . |
| WO 94/11488 | 5/1994 | WIPO . |
| WO 96/18711 | 6/1996 | WIPO . |
| WO 97/01521 | 1/1997 | WIPO . |
| WO 97/38956 | 10/1997 | WIPO . |
| WO 97/38957 | 10/1997 | WIPO . |
| WO 97/38972 | 10/1997 | WIPO . |
| WO 97/39087 | 10/1997 | WIPO . |
| WO 97/39088 | 10/1997 | WIPO . |
| WO 97/39089 | 10/1997 | WIPO . |
| WO 97/39090 | 10/1997 | WIPO . |
| WO 97/39091 | 10/1997 | WIPO . |
| WO 98/23566 | 6/1998 | WIPO . |
| WO 98/23712 | 6/1998 | WIPO . |
| WO 98/35553 | 8/1998 | WIPO . |

OTHER PUBLICATIONS

R. G. Laughlin, "The Aqueous Phase Behavior of Surfactants", *Academic Press*, N.Y. (1980), p. 347.

Finger, et al., "Detergent Alcohols—the effect of alcohol structure and molecular weight on surfactant properties", *J. Amer. Oil Chemists' Society*, vol. 44, (1967), p. 525.

Technical Bulletin, Shell Chemical Company, SC:364–80.

K. R. Wormuth, et al., "Phase Behavior of Branched Surfactants in Oil and Water", *Langmuir*, vol. 7, (1991), pp. 2048–2053.

R. Varadaraj, et al., "Fundamental Interfacial Properties of Alkyl–Branched Sulfate and Ethoxy Sulfate Surfactants Derived from Guerbet Alcohols. 1. Surface and Instantaneous Interfacial Tensions", *J. Phys. Chem.*, vol. 95 (1991), pp. 1671–1676.

R. Varadaraj, et al., "Relationship between Fundamental Interfacial Properties and Foaming in Linear and Branched Sulfate, Ethoxysulfate, and Ethoxylate Surfactants", *Journal of Colloid and Interface Science*, vol. 140, No. 1 (Nov. 1990), pp. 31–34.

R. Varadaraj, et al., "Micropolarity and Water Penetration in Micellar Aggregates of Linear and Branched Hydrocarbon Surfactants", *Langmuir*, vol. 6 (1990), pp. 1376–1378.

R. Varadaraj, et al., "Relationship between Dynamic Contact Angle and Dynamic Surface Tension Properties for Linear and Branched Ethoxylate, Ethoxysulfate, and Sulfate Surfactants", *Journal of Colloid and Interface Science*, vol. 147, No. 2 (Dec. 1991), pp. 403–406.

R. D. Swisher, "Surfactant Biodegradation", *Surfactant Science Series*, 2$^{nd}$ Ed., Marcel Dekker, Inc., vol. 18, pp. 20–29 and 34–36.

(List continued on next page.)

*Primary Examiner*—Yogendra Gupta
*Assistant Examiner*—Gregory Webb
*Attorney, Agent, or Firm*—Ian S. Robinson; Kim William Zerby

[57] ABSTRACT

This invention relates to a liquid cleaning composition comprising a surfactant system containing selected mid-chain branched surfactant and co-surfactants.

20 Claims, No Drawings

OTHER PUBLICATIONS

CEH Marketing Research Report "Detergent Alcohols" by R. F. Modler, et al., *Chemical Economics Handbook*, (1993), pp. 609.5000–609.5002.

"Alcohols, Higher Aliphatic", *Kirk Othmer's Encyclopedia of Chemical Technology*, 4th Ed., Wiley, N.Y., (1991), vol. 1, pp. 865–913.

"Liquid Fuels", *Kirk Othmer's Encyclopedia of Chemical Technology*, Wiley, N.Y., (1989), vol. 11, pp. 447–489.

"Oxo Process", *Kirk Othmer's Encyclopedia of Chemical Technology*, Wiley, N.Y., (1989), vol. 16, pp. 637–653.

"Sasol Detergent Alcohols", R&D Technical Bulletin, Sasol Alpha Olefins, (Oct. 1, 1996), pp. 1–12.

LIQUID CLEANING COMPOSITIONS CONTAINING SELECTED MID-CHAIN BRANCHED SURFACTANTS

CROSS REFERENCE

This is a continuation of PCT International Application Ser. No. PCT/US97/06473, filed Apr. 16, 1997; which claims priority to Provisional Application Ser. Nos. 60/015,521, filed Apr. 16, 1996; 60/015,523, filed Apr. 16, 1996; and 60/031,762, filed Nov. 26, 1996.

FIELD OF THE INVENTION

The present invention relates to liquid cleaning compositions (e.g., heavy duty liquid laundry detergents; hair shampoo compositions; dishwashing compositions) containing surfactants selected from mid-chain branched surfactants and co-surfactants. More particularly, the invention is directed to liquid cleaning compositions containing a surfactant system comprising a mid-chain branched surfactant in combination with one or more other co-surfactants.

BACKGROUND OF THE INVENTION

Most conventional detergent compositions contain mixtures of various detersive surfactant components. Commonly encountered surfactant components include various anionic surfactants, especially the alkyl benzene sulfonates, alkyl sulfates, alkyl alkoxy sulfates and various nonionic surfactants, such as alkyl ethoxylates and alkylphenol ethoxylates. Surfactants have found use as detergent components capable of the removal of a wide variety of soils and stains. A consistent effort however is made by detergent manufacturers to improve detersive properties of detergent compositions by providing new and improved surfactants.

A problem commonly associated with anionic surfactants is their sensitivity to cold water and/or hard water. It is the surprising finding of the present invention that in comparison to other anionic surfactant components, the mid-chain branched surfactants utilized herein provide improved cleaning performance in cold water and/or hard water. Thus, when used in combination with other surfactants in a surfactant system, they provide liquid cleaning compositions having superior cleaning properties. They are especially effective when used in laundry cleaning processes.

In addition, the present invention liquid cleaning compositions are particularly useful for personal cleansing uses, as formulated for use as hair shampoos and body washes.

An advantage of the present invention is the improved cleaning performance of liquid detergent compositions formulated containing the described mid-chain branched surfactants as a part of the total surfactant system.

BACKGROUND ART

U.S. Pat. No. 3,480,556 to deWitt, et al., Nov. 25, 1969, EP 439,316, published by Lever Jul. 31, 1991, and EP 684,300, published by Lever Nov. 29, 1995, describe beta-branched alkyl sulfates. EP 439,316 describes certain laundry detergents containing a specific commercial C14/C15 branched primary alkyl sulfate, namely LIAL 145 sulfate. This is believed to have 61% branching in the 2-position; 30% of this involves branching with a hydrocarbon chain having four or more carbon atoms. U.S. Pat. No. 3,480,556 describes mixtures of from 10 to 90 parts of a straight chain primary alkyl sulfate and from 90 to 10 parts of a beta branched (2-position branched) primary alcohol sulfate of formula:

wherein the total number of carbon atoms ranges from 12 to 20 and R1 is a straight chain alkyl radical containing 9 to 17 carbon atoms and R2 is a straight chain alkyl radical containing 1 to 9 carbon atoms (67% 2-methyl and 33% 2-ethyl branching is exemplified).

As noted hereinbefore, R. G. Laughlin in "The Aqueous Phase Behavior of Surfactants", Academic Press, N.Y. (1994) p. 347 describes the observation that as branching moves away from the 2-alkyl position towards the center of the alkyl hydrophobe there is a lowering of Krafft temperatures. See also Finger et al., "Detergent alcohols—the effect of alcohol structure and molecular weight on surfactant properties", J. Amer. Oil Chemists' Society, Vol. 44, p. 525 (1967) and Technical Bulletin, Shell Chemical Co., SC: 364–80.

EP 342,917 A, Unilever, published Nov. 23, 1989 describes laundry detergents containing a surfactant system in which the major anionic surfactant is an alkyl sulfate having an assertedly "wide range" of alkyl chain lengths (the experimental appears to involve mixing coconut and tallow chain length surfactants).

U.S. Pat. No. 4,102,823 and GB 1,399,966 describe other laundry compositions containing conventional alkyl sulfates.

G.B. Pat. No. 1,299,966, Matheson et al., published Jul. 2, 1975, discloses a detergent composition in which the surfactant system is comprised of a mixture of sodium tallow alkyl sulfate and nonionic surfactants.

Methyl-substituted sulfates include the known "isostearyl" sulfates; these are typically mixtures of isomeric sulfates having a total of 18 carbon atoms. For example, EP 401,462 A, assigned to Henkel, published Dec. 12, 1990, describes certain isostearyl alcohols and ethoxylated isostearyl alcohols and their sulfation to produce the corresponding alkyl sulfates such as sodium isostearyl sulfate. See also K. R. Wormuth and S. Zushma, Langmuir, Vol. 7, (1991), pp 2048–2053 (technical studies on a number of branched alkyl sulfates, especially the "branched Guerbet" type); R. Varadaraj et al., J. Phys. Chem., Vol. 95, (1991), pp 1671–1676 (which describes the surface tensions of a variety of "linear Guerbet" and "branched Guerbet"—class surfactants including alkyl sulfates); Varadaraj et al., J. Colloid and Interface Sci., Vol. 140, (1990), pp 31–34 (relating to foaming data for surfactants which include C12 and C13 alkyl sulfates containing 3 and 4 methyl branches, respectively); and Varadaraj et al., Langmuir, Vol. 6 (1990), pp 1376–1378 (which describes the micropolarity of aqueous micellar solutions of surfactants including branched alkyl sulfates).

"Linear Guerbet" alcohols are available from Henkel, e.g., EUTANOL G-16.

Primary akyl sulfates derived from alcohols made by Oxo reaction on propylene or n-butylene oligomers are described in U.S. Pat. No. 5,245,072 assigned to Mobil Corp. See also: U.S. Pat. No. 5,284,989, assigned to Mobil Oil Corp. (a method for producing substantially linear hydrocarbons by oligomerizing a lower olefin at elevated temperatures with constrained intermediate pore siliceous acidic zeolite), and U.S. Pat. Nos. 5,026,933 and 4,870,038, both to Mobil Oil Corp. (a process for producing substantially linear hydrocarbons by oligomerizing a lower olefin at elevated temperatures with siliceous acidic ZSM-23 zeolite).

See also: Surfactant Science Series, Marcel Dekker, N.Y. (various volumes include those entitled "Anionic Surfactants" and "Surfactant Biodegradation", the latter by R. D. Swisher, Second Edition, publ. 1987 as Vol. 18; see especially p.20–24 "Hydrophobic groups and their sources"; pp 28–29 "Alcohols", pp 34–35 "Primary Alkyl Sulfates" and pp 35–36 "Secondary Alkyl Sulfates"); and literature on "higher" or "detergent" alcohols from which alkyl sulfates are typically made, including: CEH Marketing Research Report "Detergent Alcohols" by R. F. Modler et al., Chemical Economics Handbook, 1993, 609.5000–609.5002; Kirk Othmer's Encyclopedia of Chemical Technology, 4th Edition, Wiley, N.Y., 1991, "Alcohols, Higher Aliphatic" in Vol. 1, pp 865–913 and references therein.

SUMMARY OF THE INVENTION

The present invention relates to liquid cleaning compositions comprising:

a) as part of the surfactant system, from about 0.1% to about 50% by weight of a mid-chain branched surfactant selected from the group consisting of surfactants having the formula:

$$A^b\text{—}CH_2\text{—}B$$

wherein:

(i) $A^b$ is a hydrophobic C9 to C22 (total carbons in the moiety), preferably from about C12 to about C18, mid-chain branched alkyl moiety having: (1) a longest linear carbon chain attached to the —X—B moiety in the range of from 8 to 21 carbon atoms; (2) one or more $C_1$–$C_3$ alkyl moieties branching from this longest linear carbon chain; (3) at least one of the branching alkyl moieties is attached directly to a carbon of the longest linear carbon chain at a position within the range of position 2 carbon (counting from carbon #1 which is attached to the —X—B moiety) to position ω–2 carbon (the terminal carbon minus 2 carbons, i.e., the third carbon from the end of the longest linear carbon chain); and (4) the surfactant composition has an average total number of carbon atoms in the $A^b$—X moiety in the above formula within the range of greater than 14.5 to about 17.5 (preferably from about 15 to about 17); and (ii) B is a hydrophilic moiety selected from sulfates, polyoxyalkylene (such as polyoxyethylene and polyoxypropylene), and alkoxylated sulfates;

b) as the other part of the surfactant system, from about 0.1% to about 50% by weight of one or more co-surfactants;

c) from about 1% to about 99.7% by weight of solvent; and d) from about 0.1% to about 75% by weight of liquid cleaning composition adjunct ingredients.

Also preferred are compositions wherein in the above formula the $A^b$ moiety does not have any quaternary substituted carbon atoms (i.e., 4 carbon atoms directly attached to one carbon atom).

Preferred surfactant compositions herein comprise longer alkyl chain, mid-chain branched surfactant compounds of the above formula wherein the $A^b$ moiety is a branched primary alkyl moiety having the formula:

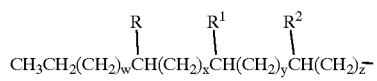

wherein the total number of carbon atoms in the branched primary alkyl moiety of this formula (including the R, $R^1$, and $R^3$ branching) is from 13 to 19; R, $R^1$, and $R^2$ are each independently selected from hydrogen and $C_1$–$C_3$ alkyl (preferably methyl), provided R, $R^1$, and $R^2$ are not all hydrogen and, when z is 0, at least R or $R^1$ is not hydrogen; w is an integer from 0 to 13; x is an integer from 0 to 13; y is an integer from 0 to 13; z is an integer from 0 to 13; and w+x+y+z is from 7 to 13.

Also preferred surfactant compositions herein comprise longer alkyl chain, mid-chain branched surfactant compounds of the above formula wherein the $A^b$ moiety is a branched primary alkyl moiety having the formula selected from:

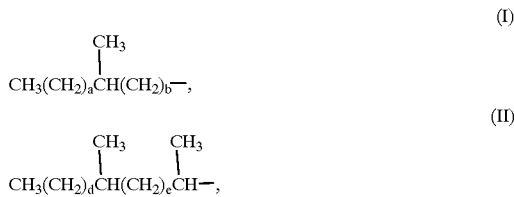

or mixtures thereof; wherein a, b, d, and e are integers, a+b is from 10 to 16, d+e is from 8 to 14 and wherein further when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when a+b=14, a is an integer from 2 to 13 and b is an integer from 1 to 12;

when a+b=15, a is an integer from 2 to 14 and b is an integer from 1 to 13;

when a+b=16, a is an integer from 2 to 15 and b is an integer from 1 to 14;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8;

when d+e=11, d is an integer from 2 to 10 and e is an integer from 1 to 9;

when d+e=12, d is an integer from 2 to 11 and e is an integer from 1 to 10;

when d+e=13, d is an integer from 2 to 12 and e is an integer from 1 to 11;

when d+e=14, d is an integer from 2 to 13 and e is an integer from 1 to 12.

Preferably, the mid-chain branched surfactant is used in the present invention liquid detergent compositions as a component of a surfactant system (i.e., the surfactant system comprises the mid-chain branched surfactant and one or more co-surfactants) wherein the mid-chain branched surfactant is present at levels of from about 0.1% to about 50%, preferably from about 1% to about 40%, most preferably from about 2% to about 30% by weight of the surfactant system. It is to be noted however that higher levels of mid-chain branched surfactant are within the present invention.

Preferably, these liquid compositions comprise a surfactant system further comprising one or more co-surfactants selected from: anionic surfactants, preferably selected from the group of alkyl alkoxylated sulfates, alkyl sulfates, and/or linear alkyl benzenesulfonate surfactants; cationic surfactants, preferably selected from quaternary ammonium surfactants; nonionic surfactants, preferably alkyl ethoxylates, alkyl polyglucosides, and/or amine (e.g., amidopropylamines) or amine oxide surfactants; amphoteric surfactants, preferably selected from betaines and/or polycarboxylates (for example polyglycinates); and zwiterionic surfactants.

Preferred liquid cleaning composition adjunct ingredients include builders, preferably water soluble builders, for example citrate/fatty acid builder systems, and detersive enzymes.

The present invention is also directed to hair shampoo compositions comprising:

a) as part of the surfactant system, from about 0.1% to about 40% by weight of an mid-chain branched surfactant as described hereinbefore;

b) as the other part of the surfactant system, from about 0.1% to about 50% by weight of one or more co-surfactants;

c) from about 1% to about 99.7% by weight of solvent; and d) from about 0.05% to about 10% by weight of one or more silicone hair conditioning agents; and e) from about 0.1% to about 75% by weight of shampoo composition adjunct ingredients.

All percentages, ratios and proportions herein are by weight of ingredients used to prepare the finished compositions unless otherwise specified. All documents cited herein are, in relevant part, incorporated herein by reference.

DETAILED DESCRIPTION OF THE INVENTION

Mid-chain Branched Surfactant

An essential component of the liquid cleaning compositions of the present invention is an mid-chain branched surfactant. The mid-chain branched surfactant is selected from the following.

The present invention relates to liquid compositions comprising mid-chain branched surfactant compounds as described herein before. In such compositions, certain points of branching (e.g., the location along the chain of the R, $R^1$, and/or $R^2$ moieties in the above formula) are preferred over other points of branching along the backbone of the surfactant. The formula below illustrates the mid-chain branching range (i.e., where points of branching occur), preferred mid-chain branching range, and more preferred mid-chain branching range for mono-methyl branched alkyl $A^b$ moieties useful according to the present invention.

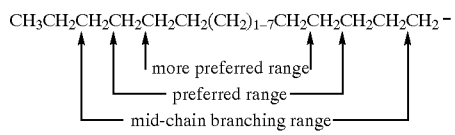

It should be noted that for the mono-methyl substituted surfactants these ranges exclude the two terminal carbon atoms of the chain and the carbon atom immediately adjacent to the —X—B group.

The formula below illustrates the mid-chain branching range, preferred mid-chain branching range, and more preferred mid-chain branching range for di-methyl substituted alkyl $A^b$ moieties useful according to the present invention.

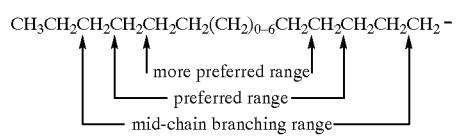

The preferred branched surfactant compositions useful in cleaning compositions according to the present invention are described in more detail hereinafter.

(1) Mid-chain Branched Primary Alkyl Sulfate Surfactants

The present invention branched surfactant compositions may comprise two or more mid-chain branched primary alkyl sulfate surfactants having the formula

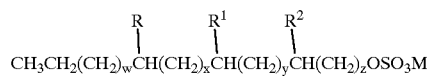

The surfactant mixtures of the present invention comprise molecules having a linear primary alkyl sulfate chain backbone (i.e., the longest linear carbon chain which includes the sulfated carbon atom). These alkyl chain backbones comprise from 12 to 19 carbon atoms; and further the molecules comprise a branched primary alkyl moiety having at least a total of 14, but not more than 20, carbon atoms. In addition, the surfactant mixture has an average total number of carbon atoms for the branched primary alkyl moieties within the range of from greater than 14.5 to about 17.5. Thus, the present invention mixtures comprise at least one branched primary alkyl sulfate surfactant compound having a longest linear carbon chain of not less than 12 carbon atoms or more than 19 carbon atoms, and the total number of carbon atoms including branching must be at least 14, and further the average total number of carbon atoms for the branched primary alkyl chains is within the range of greater than 14.5 to about 17.5.

For example, a C16 total carbon primary alkyl sulfate surfactant having 13 carbon atoms in the backbone must have 1, 2, or 3 branching units (i.e., R, $R^1$ and/or $R^3$) whereby total number of carbon atoms in the molecule is at least 16. In this example, the C16 total carbon requirement may be satisfied equally by having, for example, one propyl branching unit or three methyl branching units.

R, $R^1$, and $R^2$ are each independently selected from hydrogen and $C_1$–$C_3$ alkyl (preferably hydrogen or $C_1$–$C_2$ alkyl, more preferably hydrogen or methyl, and most preferably methyl), provided R, $R^1$, and $R^2$ are not all hydrogen. Further, when z is 1, at least R or $R^1$ is not hydrogen.

Although for the purposes of the present invention surfactant compositions the above formula does not include molecules wherein the units R, $R^1$, and $R^2$ are all hydrogen (i.e., linear non-branched primary alkyl sulfates), it is to be recognized that the present invention compositions may still further comprise some amount of linear, non-branched primary alkyl sulfate. Further, this linear non-branched primary alkyl sulfate surfactant may be present as the result of the process used to manufacture the surfactant mixture having the requisite one or more mid-chain branched primary alkyl sulfates according to the present invention, or for purposes of formulating detergent compositions some amount of linear non-branched primary alkyl sulfate may be admixed into the final product formulation.

Further it is to be similarly recognized that non-sulfated mid-chain branched alcohol may comprise some amount of the present invention compositions. Such materials may be present as the result of incomplete sulfation of the alcohol used to prepare the alkyl sulfate surfactant, or these alcohols may be separately added to the present invention detergent compositions along with a mid-chain branched alkyl sulfate surfactant according to the present invention.

M is hydrogen or a salt forming cation depending upon the method of synthesis. Examples of salt forming cations are lithium, sodium, potassium, calcium, magnesium, quaternary alkyl amines having the formula

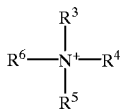

wherein $R^3$, $R^4$, $R^5$ and $R^6$ are independently hydrogen, $C_1$–$C_{22}$ alkylene, $C_4$–$C_{22}$ branched alkylene, $C_1$–$C_6$ alkanol, $C_1$–$C_{22}$ alkenylene, $C_4$–$C_{22}$ branched alkenylene, and mixtures thereof Preferred cations are ammonium ($R^3$, $R^4$, $R^5$ and $R^6$ equal hydrogen), sodium, potassium, mono-, di-, and trialkanol ammonium, and mixtures thereof. The monoalkanol ammonium compounds of the present invention have $R^3$ equal to $C_1$–$C_6$ alkanol, $R^4$, $R^5$ and $R^6$ equal to hydrogen; dialkanol ammonium compounds of the present invention have $R^3$ and $R^4$ equal to $C_1$–$C_6$ alkanol, $R^5$ and $R^6$ equal to hydrogen; trialkanol ammonium compounds of the present invention have $R^3$, $R^4$ and $R^5$ equal to $C_1$–$C_6$ alkanol, $R^6$ equal to hydrogen. Preferred alkanol ammonium salts of the present invention are the mono-, di- and tri- quaternary ammonium compounds having the formulas:

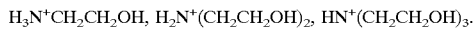

Preferred M is sodium, potassium and the $C_2$ alkanol ammonium salts listed above; most preferred is sodium.

Further regarding the above formula, w is an integer from 0 to 13; x is an integer from 0 to 13; y is an integer from 0 to 13; z is an integer of at least 1; and w+x+y+z is an integer from 8 to 14.

The preferred surfactant mixtures of the present invention have at least 0.001%, more preferably at least 5%, most preferably at least 20% by weight, of the mixture one or more branched primary alkyl sulfates having the formula

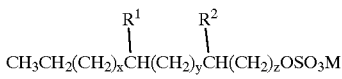

wherein the total number of carbon atoms, including branching, is from 15 to 18, and wherein further for this surfactant mixture the average total number of carbon atoms in the branched primary alkyl moieties having the above formula is with the range of greater than 14.5 to about 17.5; $R^1$ and $R^2$ are each independently hydrogen or $C_1$–$C_3$ alkyl; M is a water soluble cation; x is from 0 to 11; y is from 0 to 11; z is at least 2; and x+y+z is from 9 to 13; provided $R^1$ and $R^2$ are not both hydrogen. More preferred are compositions having at least 5% of the mixture comprising one or more mid-chain branched primary alkyl sulfates wherein x+y is equal to 9 and z is at least 2.

Preferably, the mixtures of surfactant comprise at least 5% of a mid chain branched primary alkyl sulfate having $R^1$ and $R^2$ independently hydrogen, methyl, provided $R^1$ and $R^2$ are not both hydrogen; x+y is equal to 8, 9, or 10 and z is at least 2. More preferably the mixtures of surfactant comprise at least 20% of a mid chain branched primary alkyl sulfate having $R^1$ and $R^2$ independently hydrogen, methyl, provided $R^1$ and $R^2$ are not both hydrogen; x+y is equal to 8,9, or 10 and z is at least 2.

Preferred detergent compositions according to the present invention, for example one useful for laundering fabrics, comprise from about 0.001% to about 99% of a mixture of mid-chain branched primary alkyl sulfate surfactants, said mixture comprising at least about 5% by weight of two or more mid-chain branched alkyl sulfates having the formula:

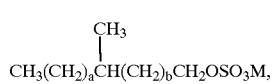

(I)

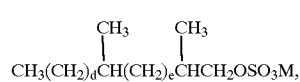

(II)

or mixtures thereof; wherein M represents one or more cations; a, b, d, and e are integers, a+b is from 10 to 16, d+e is from 8 to 14 and wherein further when a+b=10, a is an integer from 2 to 9 and b is an integer from 1 to 8;
when a+b=11, a is an integer from 2 to 10 and b is an integer from 1 to 9;
when a+b=12, a is an integer from 2 to 11 and b is an integer from 1 to 10;
when a+b=13, a is an integer from 2 to 12 and b is an integer from 1 to 11;
when a+b=14, a is an integer from 2 to 13 and b is an integer from 1 to 12;
when a+b=15, a is an integer from 2 to 14 and b is an integer from 1 to 13;
when a+b=16, a is an integer from 2 to 15 and b is an integer from 1 to 14;
when d+e=8, d is an integer from 2 to 7 and e is an integer from 1 to 6;
when d+e=9, d is an integer from 2 to 8 and e is an integer from 1 to 7;
when d+e=10, d is an integer from 2 to 9 and e is an integer from 1 to 8;
when d+e=11, d is an integer from 2 to 10 and e is an integer from 1 to 9;
when d+e=12, d is an integer from 2 to 11 and e is an integer from 1 to 10;
when d+e=13, d is an integer from 2 to 12 and e is an integer from 1 to 11;
when d+e=14, d is an integer from 2 to 13 and e is an integer from 1 to 12;
wherein further for this surfactant mixture the average total number of carbon atoms in the branched primary alkyl moieties having the above formulas is within the range of greater than 14.5 to about 17.5.

Further, the present invention surfactant composition may comprise a mixture of branched primary alkyl sulfates having the formula

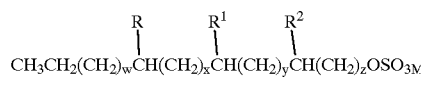

wherein the total number of carbon atoms per molecule, including branching, is from 14 to 20, and wherein further for this surfactant mixture the average total number of carbon atoms in the branched primary alkyl moieties having the above formula is within the range of greater than 14.5 to about 17.5; R, R$^1$, and R$^2$ are each independently selected from hydrogen and C$_1$–C$_3$ alkyl, provided R, R$^1$, and R$^2$ are not all hydrogen; M is a water soluble cation; w is an integer from 0 to 13; x is an integer from 0 to 13; y is an integer from 0 to 13; z is an integer of at least 1; and w+x+y+z is from 8 to 14; provided that when R$^2$ is a C$_1$–C$_3$ alkyl the ratio of surfactants having z equal to 1 to surfactants having z of 2 or greater is at least about 1:1, preferably at least about 1:5, more preferably at least about 1:10, and most preferably at least about 1:100. Also preferred are surfactant compositions, when R$^2$ is a C$_1$–C$_3$ alkyl, comprising less than about 20%, preferably less than 10%, more preferably less than 5%, most preferably less than 1%, of branched primary alkyl sulfates having the above formula wherein z equals 1.

Preferred mono-methyl branched primary alkyl sulfates are selected from the group consisting of: 3-methyl pentadecanol sulfate, 4methyl pentadecanol sulfate, 5-methyl pentadecanol sulfate, 6-methyl pentadecanol sulfate, 7-methyl pentadecanol sulfate, 8-methyl pentadecanol sulfate, 9-methyl pentadecanol sulfate, 10-methyl pentadecanol sulfate, 11-methyl pentadecanol sulfate, 12-methyl pentadecanol sulfate, 13-methyl pentadecanol sulfate, 3-methyl hexadecanol sulfate, 4methyl hexadecanol sulfate, 5-methyl hexadecanol sulfate, 6-methyl hexadecanol sulfate, 7-methyl hexadecanol sulfate, 8-methyl hexadecanol sulfate, 9-methyl hexadecanol sulfate, 10-methyl hexadecanol sulfate, 11-methyl hexadecanol sulfate, 12-methyl hexadecanol sulfate, 13-methyl hexadecanol sulfate, 14methyl hexadecanol sulfate, and mixtures thereof.

Preferred di-methyl branched primary alkyl sulfates are selected from the group consisting of: 2,3-methyl tetradecanol sulfate, 2,4methyl tetradecanol sulfate, 2,5-methyl tetradecanol sulfate, 2,6-methyl tetradecanol sulfate, 2,7-methyl tetradecanol sulfate, 2,8-methyl tetradecanol sulfate, 2,9-methyl tetradecanol sulfate, 2,10-methyl tetradecanol sulfate, 2,11-methyl tetradecanol sulfate, 2,12-methyl tetradecanol sulfate, 2,3-methyl pentadecanol sulfate, 2,&methyl pentadecanol sulfate, 2,5-methyl pentadecanol sulfate, 2,6-methyl pentadecanol sulfate, 2,7-methyl pentadecanol sulfate, 2,8-methyl pentadecanol sulfate, 2,9-methyl pentadecanol sulfate, 2,10-methyl pentadecanol sulfate, 2,1 1-methyl pentadecanol sulfate, 2,12-methyl pentadecanol sulfate, 2,13-methyl pentadecanol sulfate, and mixtures thereof.

The following branched primary alkyl sulfates comprising 16 carbon atoms and having one branching unit are examples of preferred branched surfactants useful in the present invention compositions:

5-methylpentadecylsulfate having the formula:

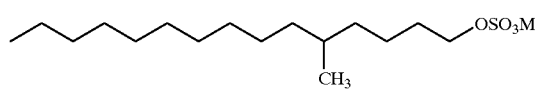

6-methylpentadecylsulfate having the formula

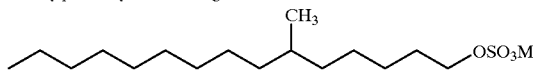

7-methylpenadecylsulfate having the formula

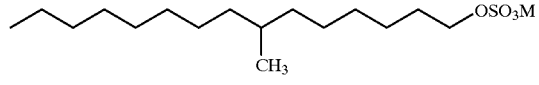

8-methylpentadecylsulfate having the formula

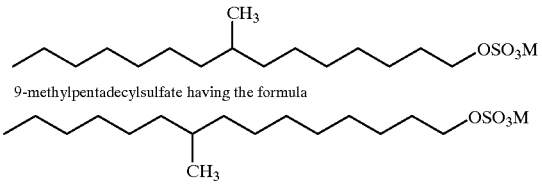

9-methylpentadecylsulfate having the formula

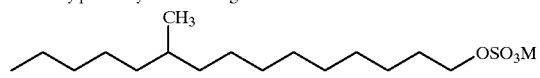

10-methylpentadecylsulfate having the formula

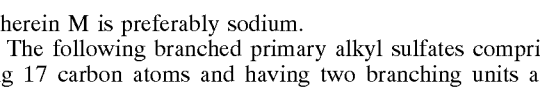

wherein M is preferably sodium.

The following branched primary alkyl sulfates comprising 17 carbon atoms and having two branching units are examples of preferred branched surfactants according to the present invention:

2,5-dimethylpentadecylsulfate having the formula:

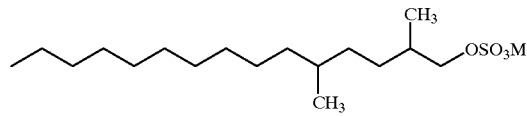

2,6-dimethylpentadecylsulfate having the formula

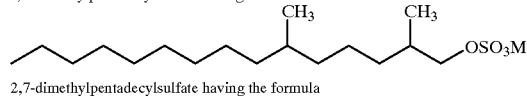

2,7-dimethylpentadecylsulfate having the formula

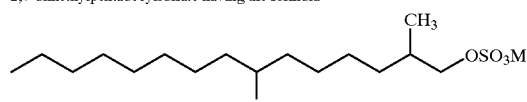

2,8-dimethylpentadecylsulfate having the formula

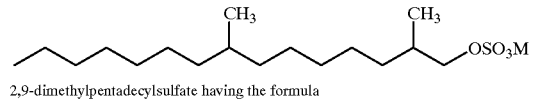

2,9-dimethylpentadecylsulfate having the formula

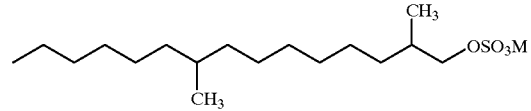

2,10-dimethylpentadecylsulfate having the formula

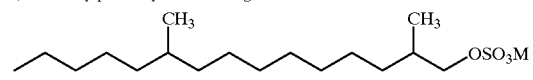

wherein M is preferably sodium.

(2) Mid-chain Branched Primary Alkyl Polyoxyalkylene Surfactants

The present invention branched surfactant compositions may comprise one or more mid-chain branched primary alkyl polyoxyalkylene surfactants having the formula

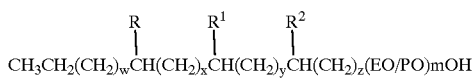

The surfactant mixtures of the present invention comprise molecules having a linear primary polyoxyalkylene chain backbone (i.e., the longest linear carbon chain which includes the alkoxylated carbon atom). These alkyl chain backbones comprise from 12 to 19 carbon atoms; and further the molecules comprise a branched primary alkyl moiety having at least a total of 14, but not more than 20, carbon atoms. In addition, the surfactant mixture has an average total number of carbon atoms for the branched primary alkyl moieties within the range of from greater than 14.5 to about 17.5. Thus, the present invention mixtures comprise at least one polyoxyalkylene compound having a longest linear carbon chain of not less than 12 carbon atoms or more than 19 carbon atoms, and the total number of carbon atoms including branching must be at least 14, and further the average total number of carbon atoms for the branched primary alkyl chains is within the range of greater than 14.5 to about 17.5.

For example, a C16 total carbon (in the alkyl chain) primary polyoxyalkylene surfactant having 15 carbon atoms in the backbone must have a methyl branching unit (either R, $R^1$ or $R^2$ is methyl) whereby the total number of carbon atoms in the molecule is 16.

R, $R^1$, and $R^2$ are each independently selected from hydrogen and $C_1$–$C_3$ alkyl (preferably hydrogen or $C_1$–$C_2$ alkyl, more preferably hydrogen or methyl, and most preferably methyl), provided R, $R^1$, and $R^2$ are not all hydrogen. Further, when z is 1, at least R or $R^1$ is not hydrogen.

Although for the purposes of the present invention surfactant compositions the above formula does not include molecules wherein the units R, $R^1$, and $R^2$ are all hydrogen (i.e., linear non-branched primary polyoxyalkylenes), it is to be recognized that the present invention compositions may still further comprise some amount of linear, non-branched primary polyoxyalkylene. Further, this linear non-branched primary polyoxyalkylene surfactant may be present as the result of the process used to manufacture the surfactant mixture having the requisite mid-chain branched primary polyoxyalkylenes according to the present invention, or for purposes of formulating detergent compositions some amount of linear non-branched primary polyoxyalkylene may be admixed into the final product formulation.

Further it is to be similarly recognized that non-alkoxylated mid-chain branched alcohol may comprise some amount of the present invention polyoxyalkylene-containing compositions. Such materials may be present as the result of incomplete alkoxylation of the alcohol used to prepare the polyoxyalkylene surfactant, or these alcohols may be separately added to the present invention detergent compositions along with a mid-chain branched polyoxyalkylene surfactant according to the present invention.

Further regarding the above formula, w is an integer from 0 to 13; x is an integer from 0 to 13; y is an integer from 0 to 13; z is an integer of at least 1; and w+x+y+z is an integer from 8 to 14.

EO/PO are alkoxy moieties, preferably selected from ethoxy, propoxy, and mixed ethoxy/propoxy groups, most preferably ethoxy, wherein m is at least about 1, preferably within the range of from about 3 to about 30, more preferably from about 5 to about 20, and most preferably from about 5 to about 15. The $(EO/PO)_m$ moiety may be either a distribution with average degree of alkoxylation (e.g., ethoxylation and/or propoxylation) corresponding to m, or it may be a single specific chain with alkoxylation (e.g., ethoxylation and/or propoxylation) of exactly the number of units corresponding to m.

The preferred surfactant mixtures of the present invention have at least 0.001%, more preferably at least 5%, most preferably at least 20% by weight, of the mixture one or more mid-chain branched primary alkyl polyoxyalkylenes having the formula

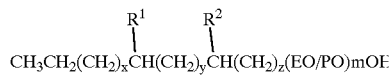

wherein the total number of carbon atoms, including branching, is from 15 to 18, and wherein further for this surfactant mixture the average total number of carbon atoms in the branched primary alkyl moieties having the above formula is within the range of greater than 14.5 to about 17.5; $R^1$ and $R^2$ are each independently hydrogen or $C_1$–$C_3$ alkyl; x is from 0 to 11; y is from 0 to 11; z is at least 2; and x+y+z is from 9 to 13; provided $R^1$ and $R^2$ are not both hydrogen; and EO/PO are alkoxy moieties selected from ethoxy, propoxy, and mixed ethoxy/propoxy groups, wherein m is at least about 1, preferably within the range of from about 3 to about 30, more preferably from about 5 to about 20, and most preferably from about 5 to about 15. More preferred are compositions having at least 5% of the mixture comprising one or more mid-chain branched primary polyoxyalkylenes wherein z is at least 2.

Preferably, the mixtures of surfactant comprise at least 5%, preferably at least about 20%, of a mid chain branched primary alkyl polyoxyalkylene having $R^1$ and $R^2$ independently hydrogen or methyl, provided $R^1$ and $R^2$ are not both hydrogen; x+y is equal to 8, 9 or 10 and z is at least 2.

Preferred detergent compositions according to the present invention, for example one useful for laundering fabrics, comprise from about 0.001% to about 99% of a mixture of mid-chain branched primary alkyl polyoxyalkylene surfactants, said mixture comprising at least about 2% by weight of one or more mid-chain branched alkyl polyoxyalkylenes having the formula:

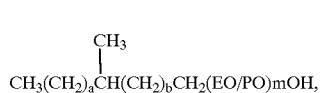

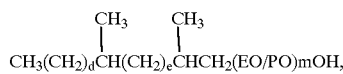

or mixtures thereof; wherein a, b, d, and e are integers, a+b is from 10 to 16, d+e is from 8 to 14 and wherein further
when a+b=10, a is an integer from 2 to 9 and b is an integer from 1 to 8;
when a+b=11, a is an integer from 2 to 10 and b is an integer from 1 to 9;
when a+b=12, a is an integer from 2 to 11 and b is an integer from 1 to 10;
when a+b=13, a is an integer from 2to 12 and b is an integer from 1 to 11;
when a+b=14, a is an integer from 2 to 13 and b is an integer from 1 to 12;
when a+b=15, a is an integer from 2 to 14 and b is an integer from 1 to 13;
when a+b=16, a is an integer from 2 to 15 and b is an integer from 1 to 14;
when d+e=8, d is an integer from 2 to 7 and e is an integer from 1 to 6;
when d+e=9, d is an integer from 2 to 8 and e is an integer from 1 to 7;
when d+e=10, d is an integer from 2 to 9 and e is an integer from 1 to 8;
when d+e=11, d is an integer from 2 to 10 and e is an integer from 1 to 9;

when d+e=12, d is an integer from 2 to 11 and e is an integer from 1 to 10;
when d+e=13, d is an integer from 2 to 12 and e is an integer from 1 to 11;
when d+e=14, d is an integer from 2 to 13 and e is an integer from 1 to 12;
and wherein further for this surfactant mixture the average total number of carbon atoms in the branched primary allyl moieties having the above formulas is within the range of greater than 14.5 to about 17.5; and EO/PO are alkoxy moieties selected from ethoxy, propoxy, and mixed ethoxy/propoxy groups, wherein m is at least about 1, preferably within the range of from about 3 to about 30, more preferably from about 5 to about 20, and most preferably from about 5 to about 15.

Further, the present invention surfactant composition may comprise a mixture of branched primary alkyl polyoxyalkylenes having the formula

wherein the total number of carbon atoms per molecule, including branching, is from 14 to 20, and wherein further for this surfactant mixture the average total number of carbon atoms in the branched primary alkyl moieties having the above formula is within the range of greater than 14.5 to about 17.5; R, $R^1$, and $R^2$ are each independently selected from hydrogen and $C_1$–$C_3$ alkyl, provided R, $R^1$, and $R^2$ are not all hydrogen; w is an integer from 0 to 13; x is an integer from 0 to 13; y is an integer from 0 to 13; z is an integer of at least 1; w+x+y+z is from 8 to 14; EO/PO are alkoxy moieties, preferably selected from ethoxy, propoxy, and mixed ethoxy/propoxy groups, wherein m is at least about 1, preferably within the range of from about 3 to about 30, more preferably from about 5 to about 20, and most preferably from about 5 to about 15; provided that when $R^2$ is $C_1$–$C_3$ alkyl the ratio of surfactants having z equal to 2 or greater to surfactants having z of 1 is at least about 1:1, preferably at least about 1.5:1, more preferably at least about 3:1, and most preferably at least about 4:1. Also preferred are surfactant compositions when $R^2$ is $C_1$–$C_3$ alkyl comprising less than about 50%, preferably less than about 40%, more preferably less than about 25%, most preferably less than about 20%, of branched primary alkyl polyoxyalkylene having the above formula wherein z equals 1.

Preferred mono-methyl branched primary alkyl ethoxylates are selected from the group consisting of: 3-methyl pentadecanol ethoxylate, 4methyl pentadecanol ethoxylate, 5-methyl pentadecanol ethoxylate, 6-methyl pentadecanol ethoxylate, 7-methyl pentadecanol ethoxylate, 8-methyl pentadecanol ethoxylate, 9-methyl pentadecanol ethoxylate, 10-methyl pentadecanol ethoxylate, 11-methyl pentadecanol ethoxylate, 12-methyl pentadecanol ethoxylate, 13-methyl pentadecanol ethoxylate, 3-methyl hexadecanol ethoxylate, 4methyl hexadecanol ethoxylate, 5-methyl hexadecanol ethoxylate, 6-methyl hexadecanol ethoxylate, 7-methyl hexadecanol ethoxylate, 8-methyl hexadecanol ethoxylate, 9-methyl hexadecanol ethoxylate, 10-methyl hexadecanol ethoxylate, 11-methyl hexadecanol ethoxylate, 12-methyl hexadecanol ethoxylate, 13-methyl hexadecanol ethoxylate, 14-methyl hexadecanol ethoxylate, and mixtures thereof, wherein the compounds are ethoxylated with an average degree of ethoxylation of from about 5 to about 15.

Preferred di-methyl branched primary alkyl ethoxylates selected from the group consisting of: 2,3-methyl tetradecanol ethoxylate, 2,4methyl tetradecanol ethoxylate, 2,5-methyl tetradecanol ethoxylate, 2,6-methyl tetradecanol ethoxylate, 2,7-methyl tetradecanol ethoxylate, 2,8-methyl tetradecanol ethoxylate, 2,9-methyl tetradecanol ethoxylate, 2,10-methyl tetradecanol ethoxylate, 2,11-methyl tetradecanol ethoxylate, 2,12-methyl tetradecanol ethoxylate, 2,3-methyl pentadecanol ethoxylate, 2,4-methyl pentadecanol ethoxylate, 2,5-methyl pentadecanol ethoxylate, 2,6-methyl pentadecanol ethoxylate, 2,7-methyl pentadecanol ethoxylate, 2,8-methyl pentadecanol ethoxylate, 2,9-methyl pentadecanol ethoxylate, 2,10-methyl pentadecanol ethoxylate, 2,11-methyl pentadecanol ethoxylate, 2,12-methyl pentadecanol ethoxylate, 2,13-methyl pentadecanol ethoxylate, and mixtures thereof, wherein the compounds are ethoxylated with an average degree of ethoxylation of from about 5 to about 15.

(3) Mid-chain Branched Primary Alkyl Alkoxylated Sulfate Surfactants

The present invention branched surfactant compositions may comprise one or more (preferably a mixture of two or more) mid-chain branched primary alkyl alkoxylated sulfates having the formula:

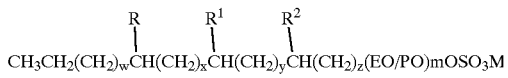

The surfactant mixtures of the present invention comprise molecules having a linear primary alkoxylated sulfate chain backbone (i.e., the longest linear carbon chain which includes the alkoxy-sulfated carbon atom). These alkyl chain backbones comprise from 12 to 19 carbon atoms; and further the molecules comprise a branched primary alkyl moiety having at least a total of 14, but not more than 20, carbon atoms. In addition, the surfactant mixture has an average total number of carbon atoms for the branched primary alkyl moieties within the range of from greater than 14.5 to about 17.5. Thus, the present invention mixtures comprise at least one alkoxylated sulfate compound having a longest linear carbon chain of not less than 12 carbon atoms or more than 19 carbon atoms, and the total number of carbon atoms including branching must be at least 14, and further the average total number of carbon atoms for the branched primary alkyl chains is within the range of greater than 14.5 to about 17.5.

For example, a C16 total carbon (in the alkyl chain) primary alkyl alkoxylated sulfate surfactant having 15 carbon atoms in the backbone must have a methyl branching unit (either R, $R^1$ or $R^2$ is methyl) whereby the total number of carbon atoms in the primary alkyl moiety of the molecule is 16.

R, $R^1$, and $R^2$ are each independently selected from hydrogen and $C_1$–$C_3$ alkyl (preferably hydrogen or $C_1$–$C_2$ alkyl, more preferably hydrogen or methyl, and most preferably methyl), provided R, $R^1$, and $R^2$ are not all hydrogen. Further, when z is 1, at least R or $R^1$ is not hydrogen.

Although for the purposes of the present invention surfactant compositions the above formula does not include molecules wherein the units R, $R^1$, and $R^2$ are all hydrogen (i.e., linear non-branched primary alkoxylated sulfates), it is to be recognized that the present invention compositions may still further comprise some amount of linear, non-branched primary alkoxylated sulfate. Further, this linear non-branched primary alkoxylated sulfate surfactant may be present as the result of the process used to manufacture the surfactant mixture having the requisite mid-chain branched primary alkoxylated sulfates according to the present invention, or for purposes of formulating detergent compositions some amount of linear non-branched primary alkoxylated sulfate may be admixed into the final product formulation.

It is also to be recognized that some amount of mid-chain branched alkyl sulfate may be present in the compositions. This is typically the result of sulfation of non-alkoxylated alcohol remaining following incomplete alkoxylation of the mid-chain branched alcohol used to prepare the alkoxylated sulfate useful herein. It is to be recognized, however, that separate addition of such mid-chain branched alkyl sulfates is also contemplated by the present invention compositions.

Further it is to be similarly recognized that non-sulfated mid-chain branched alcohol (including polyoxyalkylene alcohols) may comprise some amount of the present invention alkoxylated sulfate-containing compositions. Such materials may be present as the result of incomplete sulfation of the alcohol (alkoxylated or non-alkoxylated) used to prepare the alkoxylated sulfate surfactant, or these alcohols may be separately added to the present invention detergent compositions along with a mid-chain branched alkoxylated sulfate surfactant according to the present invention.

M is as described hereinbefore.

Further regarding the above formula, w is an integer from 0 to 13; x is an integer from 0 to 13; y is an integer from 0 to 13; z is an integer of at least 1; and w+x+y+z is an integer from 8 to 14.

EO/PO are alkoxy moieties, preferably selected from ethoxy, propoxy, and mixed ethoxy/propoxy groups, wherein m is at least about 0.01, preferably within the range of from about 0.1 to about 30, more preferably from about 0.5 to about 10, and most preferably from about 1 to about 5. The $(EO/PO)_m$ moiety may be either a distribution with average degree of alkoxylation (e.g., ethoxylation and/or propoxylation) corresponding to m, or it may be a single specific chain with alkoxylation (e.g., ethoxylation and/or propoxylation) of exactly the number of units corresponding to m.

The preferred surfactant mixtures of the present invention have at least 0.001%, more preferably at least 5%, most preferably at least 20% by weight, of the mixture one or more mid-chain branched primary alkyl alkoxylated sulfates having the formula

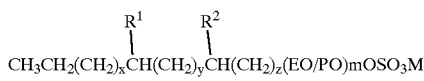

wherein the total number of carbon atoms, including branching, is from 15 to 18, and wherein further for this surfactant mixture the average total number of carbon atoms in the branched primary alkyl moieties having the above formula is within the range of greater than 14.5 to about 17.5; $R^1$ and $R^2$ are each independently hydrogen or $C_1$–$C_3$ alkyl; M is a water soluble cation; x is from 0 to 11; y is from 0 to 11; z is at least 2; and x+y+z is from 9 to 13; provided $R^1$ and $R^2$ are not both hydrogen; and EO/PO are alkoxy moieties selected from ethoxy, propoxy, and mixed ethoxy/propoxy groups, wherein m is at least about 0.01, preferably within the range of from about 0.1 to about 30, more preferably from about 0.5 to about 10, and most preferably from about 1 to about 5. More preferred are compositions having at least 5% of the mixture comprising one or more mid-chain branched primary alkoxylated sulfates wherein z is at least 2.

Preferably, the mixtures of surfactant comprise at least 5%, preferably at least about 20%, of a mid chain branched primary alkyl alkoxylated sulfate having $R^1$ and $R^2$ independently hydrogen or methyl, provided $R^1$ and $R^2$ are not both hydrogen; x+y is equal to 8, 9 or 10 and z is at least 2.

Preferred detergent compositions according to the present invention, for example one useful for laundering fabrics, comprise from about 0.001% to about 99% of a mixture of mid-chain branched primary alkyl alkoxylated sulfate surfactants, said mixture comprising at least about 5% by weight of one or more mid-chain branched alkyl alkoxylated sulfates having the formula:

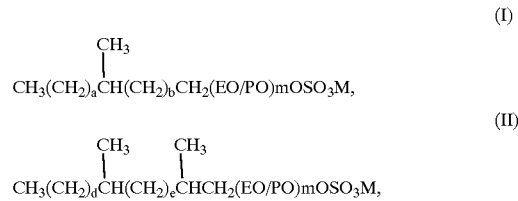

or mixtures thereof; wherein M represents one or more cations; a, b, d, and e are integers, a+b is from 10 to 16, d+e is from 8 to 14 and wherein further when a+b=10, a is an integer from 2 to 9 and b is an integer from 1 to 8;

when a+b=11, a is an integer from 2 to 10 and b is an integer from 1 to 9;

when a+b=12, a is an integer from 2 to 11 and b is an integer from 1 to 10;

when a+b=13, a is an integer from 2 to 12 and b is an integer from 1 to 11;

when a+b=14, a is an integer from 2 to 13 and b is an integer from 1 to 12;

when a+b=15, a is an integer from 2 to 14 and b is an integer from 1 to 13;

when a+b=16, a is an integer from 2 to 15 and b is an integer from 1 to 14;

when d+e=8, d is an integer from 2 to 7 and e is an integer from 1 to 6;

when d+e=9, d is an integer from 2 to 8 and e is an integer from 1 to 7;

when d+e=10, d is an integer from 2 to 9 and e is an integer from 1 to 8;

when d+e=11, d is an integer from 2 to 10 and e is an integer from 1 to 9;

when d+e=12, d is an integer from 2 to 11 and e is an integer from 1 to 10;

when d+e=13, d is an integer from 2 to 12 and e is an integer from 1 to 11;

when d+e=14, d is an integer from 2 to 13 and e is an integer from 1 to 12;

and wherein further for this surfactant mixture the average total number of carbon atoms in the branched primary alkyl moieties having the above formulas is within the range of greater than 14.5 to about 17.5; and EO/PO are alkoxy moieties selected from ethoxy, propoxy, and mixed ethoxy/propoxy groups, wherein m is at least about 0.01, preferably within the range of from about 0.1 to about 30, more preferably from about 0.5 to about 10, and most preferably from about 1 to about 5.

Further, the present invention surfactant composition may comprise a mixture of branched primary alkyl alkoxylated sulfates having the formula

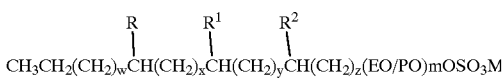

wherein the total number of carbon atoms per molecule, including branching, is from 14 to 20, and wherein further for this surfactant mixture the average total number of carbon atoms in the branched primary alkyl moieties having the above formula is within the range of greater than 14.5 to about 17.5; R, $R^1$, and $R^2$ are each independently selected from hydrogen and $C_1$–$C_3$ alkyl, provided R, $R^1$, and $R^2$ are not all hydrogen; M is a water soluble cation; w is an integer from 0 to 13; x is an integer from 0 to 13; y is an integer from 0 to 13; z is an integer of at least 1; w+x+y+z is from 8 to 14; EO/PO are alkoxy moieties, preferably selected from ethoxy, propoxy, and mixed ethoxy/propoxy groups, wherein m is at least about 0.01, preferably within the range of from about 0.1 to about 30, more preferably from about 0.5 to about 10, and most preferably from about 1 to about 5; provided that when $R^2$ is $C_1$–$C_3$ alkyl the ratio of surfactants having z equal to 2 or greater to surfactants having z of 1 is at least about 1:1, preferably at least about 1.5:1, more preferably at least about 3:1, and most preferably at least about 4:1. Also preferred are surfactant compositions when $R^2$ is $C_1$–$C_3$ alkyl comprising less than about 50%, preferably less than about 40%, more preferably less than about 25%, most preferably less than about 20%, of branched primary alkyl alkoxylated sulfate having the above formula wherein z equals 1.

Preferred mono-methyl branched primary alkyl ethoxylated sulfates are selected from the group consisting of: 3-methyl pentadecanol ethoxylated sulfate, 4-methyl pentadecanol ethoxylated sulfate, 5-methyl pentadecanol ethoxylated sulfate, 6-methyl pentadecanol ethoxylated sulfate, 7-methyl pentadecanol ethoxylated sulfate, 8-methyl pentadecanol ethoxylated sulfate, 9-methyl pentadecanol ethoxylated sulfate, 10-methyl pentadecanol ethoxylated sulfate, 11-methyl pentadecanol ethoxylated sulfate, 12-methyl pentadecanol ethoxylated sulfate, 13-methyl pentadecanol ethoxylated sulfate, 3-methyl hexadecanol ethoxylated sulfate, 4-methyl hexadecanol ethoxylated sulfate, 5-methyl hexadecanol ethoxylated sulfate, 6-methyl hexadecanol ethoxylated sulfate, 7-methyl hexadecanol ethoxylated sulfate, 8-methyl hexadecanol ethoxylated sulfate, 9-methyl hexadecanol ethoxylated sulfate, 10-methyl hexadecanol ethoxylated sulfate, 11-methyl hexadecanol ethoxylated sulfate, 12-methyl hexadecanol ethoxylated sulfate, 13-methyl hexadecanol ethoxylated sulfate, 14-methyl hexadecanol ethoxylated sulfate, and mixtures thereof, wherein the compounds are ethoxylated with an average degree of ethoxylation of from about 0.1 to about 10.

Preferred di-methyl branched primary alkyl ethoxylated sulfates selected from the group consisting of: 2,3-methyl tetradecanol ethoxylated sulfate, 2,4-methyl tetradecanol ethoxylated sulfate, 2,5-methyl tetradecanol ethoxylated sulfate, 2,6-methyl tetradecanol ethoxylated sulfate, 2,7-methyl tetradecanol ethoxylated sulfate, 2,8-methyl tetradecanol ethoxylated sulfate, 2,9-methyl tetradecanol ethoxylated sulfate, 2,10-methyl tetradecanol ethoxylated sulfate, 2,11-methyl tetradecanol ethoxylated sulfate, 2,12-methyl tetradecanol ethoxylated sulfate, 2,3-methyl pentadecanol ethoxylated sulfate, 2,4methyl pentadecanol ethoxylated sulfate, 2,5-methyl pentadecanol ethoxylated sulfate, 2,6-methyl pentadecanol ethoxylated sulfate, 2,7-methyl pentadecanol ethoxylated sulfate, 2,8-methyl pentadecanol ethoxylated sulfate, 2,9-methyl pentadecanol ethoxylated sulfate, 2,10-methyl pentadecanol ethoxylated sulfate, 2,11-methyl pentadecanol ethoxylated sulfate, 2,12-methyl pentadecanol ethoxylated sulfate, 2,13-methyl pentadecanol ethoxylated sulfate, and mixtures thereof, wherein the compounds are ethoxylated with an average degree of ethoxylation of from about 0.1 to about 10.

Preparation of Mid-chain Branched Surfactants

The following reaction scheme outlines a general approach to the preparation of the mid-chain branched primary alcohol useful for alkoxylating and/or sulfating to prepare the mid-chain branched primary alkyl surfactants of the present invention.

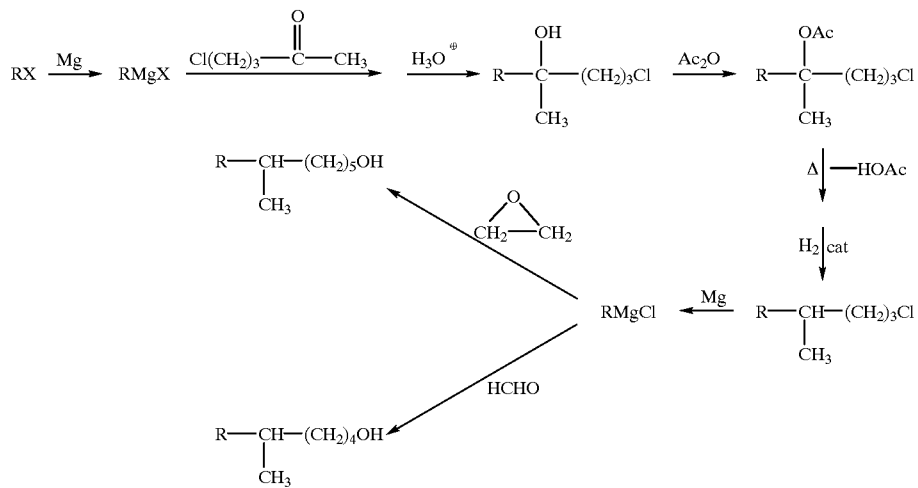

An alkyl halide is converted to a Grignard reagent and the Grignard is reacted with a haloketone. After conventional acid hydrolysis, acetylation and thermal elimination of acetic acid, an intermediate olefin is produced (not shown in the scheme) which is hydrogenated forthwith using any convenient hydrogenation catalyst such as Pd/C.

This route is favorable over others in that the branch, in this illustration a 5-methyl branch, is introduced early in the reaction sequence.

Formylation of the alkyl halide resulting from the first hydrogenation step yields alcohol product, as shown in the scheme. This can be alkoxylated using standard techniques and/or sulfated using any convenient sulfating agent, e.g., chlorosulfonic acid, SO3/air, or oleum, to yield the final branched primary alkyl surfactant. There is flexibility to extend the branching one additional carbon beyond that which is achieved by a single formylation. Such extension can, for example, be accomplished by reaction with ethylene oxide. See "Grignard Reactions of Nonmetallic Substances", M. S. Kharasch and O. Reinmuth, Prentice-Hall, N.Y., 1954; *J. Org. Chem.*, J. Cason and W. R. Winans, Vol. 15 (1950), pp 139–147; *J. Org Chem.*, J. Cason et al., Vol. 13 (1948), pp 239–248; *J. Org Chem.*, J. Cason et al., Vol. 14 (1949), pp 147–154; and *J. Org Chem.*, J. Cason et al., Vol. 15 (1950), pp 135–138 all of which are incorporated herein by reference.

In variations of the above procedure, alternate haloketones or Grignard reagents may be used. PBr3 halogenation of the alcohol from formylation or ethoxylation can be used to accomplish an iterative chain extension.

The preferred mid-chained branched primary alkyl alkoxylated sulfates (as well as the polyoxyalkylenes and alkyl sulfates, by choosing to only alkoxylate or sulfate the intermediate alcohol produced) of the present invention can also be readily prepared as follows:

Any alternative synthetic procedure in accordance with the invention may be used to prepare the branched primary alkyl surfactants. The mid-chain branched primary alkyl surfactants may, in addition be synthesized or formulated in the presence of the conventional homologs, for example any of those which may be formed in an industrial process which produces 2-alkyl branching as a result of hydroformylation. Mid-chain branched surfactant mixtures of the present invention are routinely added to other known commercial alkyl surfactants contained in the final laundry product formulation.

In certain preferred embodiments of the surfactant mixtures of the present invention, especially those derived from fossil fuel sources involving commercial processes, comprise at least 1 mid-chain branched primary alkyl surfactant, preferably at least 2, more preferably at least 5, most preferably at least 8.

Particularly suitable for preparation of certain surfactant mixtures of the present invention are "oxo" reactions wherein a branched chain olefin is subjected to catalytic isomerization and hydroformylation prior to alkoxylation and/or sulfation. The preferred processes resulting in such mixtures utilize fossil fuels as the starting material feedstock. Preferred processes utilize Oxo reaction on linear olefins (alpha or internal) with a limited amount of branching. Suitable olefins may be made by dimerization of linear alpha or internal olefins, by controlled oligomerization of low molecular weight linear olefins, by skeletal rearrangement of detergent range olefins, by dehydrogenation/skeletal rearrangement of detergent range paraffins, or by Fischer-Tropsch reaction. These reactions will in general be controlled to:

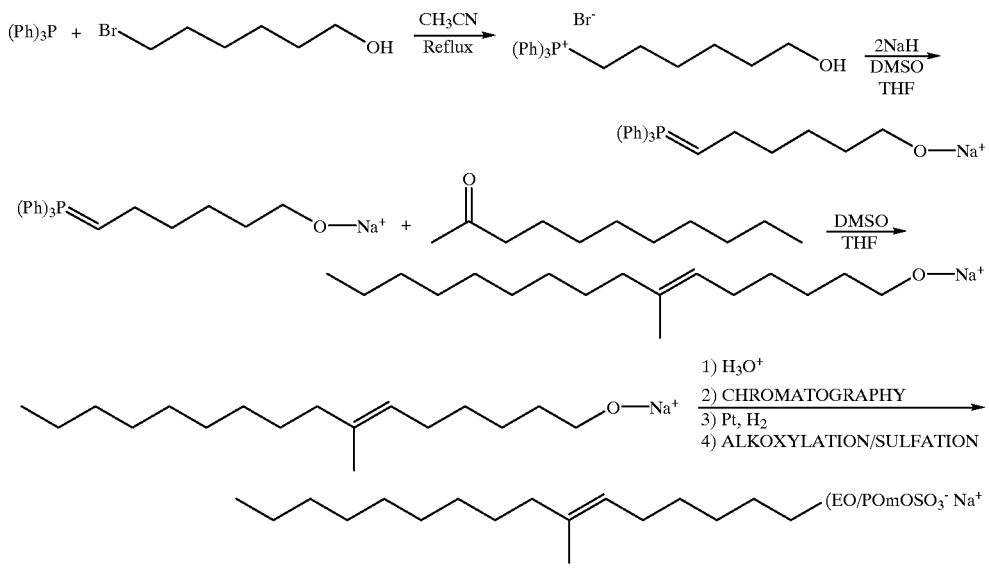

A conventional bromoalcohol is reacted with triphenylphosphine followed by sodium hydride, suitably in dimethylsulfoxide/tetrahydrofuran, to form a Wittig adduct. The Wittig adduct is reacted with an alpha methyl ketone, forming an internally unsaturated methyl-branched alcoholate. Hydrogenation followed by alkoxylation and/or sulfation yields the desired mid-chain branched primary alkyl surfactant. Although the Wittig approach does not allow the practitioner to extend the hydrocarbon chain, as in the Grignard sequence, the Wittig typically affords higher yields. See *Agricultural and Biological Chemistry*, M. Horiike et al., vol. 42 (1978), pp 1963–1965 included herein by reference.

1) give a large proportion of olefins in the desired detergent range (while allowing for the addition of a carbon atom in the subsequent Oxo reaction),
2) produce a limited number of branches, preferably mid-chain,
3) produce $C_1$–$C_3$ branches, more preferably ethyl, most preferably methyl,
4) limit or eliminate gem dialkyl branching i.e. to avoid formation of quaternary carbon atoms. The suitable olefins can undergo Oxo reaction to give primary alcohols either directly or indirectly through the corresponding aldehydes. When an internal olefin is used, an Oxo catalyst is normally used which is capable of prior pre-isomerization of internal olefins primarily to alpha olefins. While a separately catalyzed (i.e. non-Oxo) internal to alpha isomerization could be effected, this is optional. On the other hand, if the olefin-forming step itself results directly in an alpha olefin (e.g. with high pressure Fischer-Tropsch olefins of detergent range), then use of a non-isomerizing Oxo catalyst is not only possible, but preferred.

The process described herein above gives the more preferred 5-methyl-hexadecyl surfactants in higher yield than the less preferred 2,4-dimethylpentadecyl surfactants. This mixture is desirable under the metes and bounds of the present invention in that each product comprises at total of 17 carbon atoms with linear alkyl chains having at least 13 carbon atoms.

The following examples provide methods for synthesizing various compounds useful in the present invention compositions.

EXAMPLE I

Preparation of Sodium 7-Methyhexadecyl Ethoxylate (E2) and Ethoxylated Sulfate

Synthesis of (6-hydroxyhexyl) Triphenylphosphonium Bromide

Into a 5 L, 3 neck round bottom flask fitted with nitrogen inlet, condenser, thermometer, mechanical stirring and nitrogen outlet is added 6-bromo-1-hexanol (500 g, 2.76 mol), triphenylphosphine (768 g, 2.9mol) and acetonitrile (1800 ml) under nitrogen. The reaction mixture is heated to reflux for 72 hrs. The reaction mixture is cooled to room temperature and transferred into a 5 L beaker. The product is recrystallized from anhydrous ethyl ether (1.5 L) at 10° C. Vacuum filtration followed by washing with ethyl ether and drying in a vacuum oven at 50° C. for 2 hrs. gives 1140 g of the desired product as white crystals.

Synthesis of 7- methylhexadecene-1-ol

Into a dried 5 L, 3 neck round bottom flask fitted with mechanical stirring, nitrogen inlet, dropping funnel, thermometer and nitrogen outlet is added 70.2 g of 60% sodium hydride (1.76 mol) in mineral oil. The mineral oil is removed by washing with hexanes. Anhydrous dimethyl sulfoxide (500 ml) is added to the flask and the mixture is heated to 70° C. until evolution of hydrogen stops. The reaction mixture is cooled to room temperature followed by addition of 1 L of anhydrous tetrahydrofuran. (6-hydroxyhexyl) triphenylphosphonium bromide (443.4 g, 1 mol) is slurried with warm anhydrous dimethyl sulfoxide (50° C., 500 ml) and slowly added to the reaction mixture through the dropping funnel while keeping it at 25–30° C. The mixture is stirred for 30 minutes at room temperature at which time 2-undecanone (187 g, 1.1 mol) is slowly added through a dropping funnel. Reaction is slightly exothermic and cooling is needed to maintain 25–30° C. The mixture is stirred for 18 hr. and then poured into a 5 L beaker containing 1 L purified water with stirring. The oil phase (top) is allowed to separate out in a separatory funnel and the water phase is removed. The water phase is washed with hexanes (500 ml) and the organic phase is separated and combined with the oil phase from the water wash. The organic mixture is then extracted with water 3 times (500 ml each) followed by vacuum distillation to collect the clear, oily product (132 g) at 140C and 1 mm Hg.

Hydrogenation of 7- methylhexadecene-1-ol

Into a 3 L rocking autoclave liner is added 7-methylhexadecene-1-ol (130 g, 0.508 mol), methanol (300 ml) and platinum on carbon (10% by weight, 35 g). The mixture is hydrogenated at 180° C. under 1200 psig of hydrogen for 13 hrs., cooled and vacuum filtered thru Celite 545 with washing of the Celite 545, suitably with methylene chloride. If needed, the filtration can be repeated to eliminate traces of Pt catalyst, and magnesium sulfate can be used to dry the product. The solution of product is concentrated on a rotary evaporator to obtain a clear oil (124 g).

Alkoxylation of 7-methylhexadecanol

Into a dried 1 L 3 neck round bottom flask fitted with a nitrogen inlet, mechanical stirrer, and a y-tube fitted with a thermometer and a gas outlet is added the alcohol from the preceeding step. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to two equivalents of ethylene oxide) has been added, nitrogen is swept through the apparatus for 20–30 minutes as the sample is allowed to cool. The desired 7-methylhexadecyl ethoxylate (average of 2 ethoxylates per molecule) product is then collected.

Sulfation of 7-methylhexadecyl ethoxylate (E2)

Into a dried 1 L 3 neck round bottom flask fitted with a nitrogen inlet, dropping funnel, thermometer, mechanical stirring and nitrogen outlet is added chloroform and 7-methylhexadecyl ethoxylate (E2) from the preceeding step. Chlorosulfonic acid is slowly added to the stirred mixture while maintaining 25–30° C. temperature with an ice bath. Once HCl evolution has stopped slowly add sodium methoxide (25% in methanol) while keeping temperature at 25–30° C. until a aliquot at 5% concentration in water maintains a pH of 10.5. To the mixture is added hot ethanol (55° C.) and vacuum filtered immediately. The filtrate is concentrated to a slurry on a rotary evaporator, cooled and then poured into ethyl ether. The mixture is chilled to 5° C. and vacuum filtered to provide the desired 7-methylhexadecyl ethoxylate (average of 2 ethoxylates per molecule) sulfate, sodium salt, product

EXAMPLE II

Synthesis of Sodium 7-methylpentadecyl ethoxylate (E5) and ethoxylated Sulfate

Synthesis of (6-hydroxyhexyl) Triphenylphosphonium Bromide

Into a 5 L, 3 neck round bottom flask fitted with nitrogen inlet, condenser, thermometer, mechanical stirring and nitrogen outlet is added 6-bromo-1-hexanol (500 g, 2.76 mol), triphenylphosphine (768 g, 2.9 mol) and acetonitrile (1800 Ml) under nitrogen. The reaction mixture is heated to reflux for 72 hrs. The reaction mixture is cooled to room temperature and transferred into a SL beaker. The product is recrystallized from anhydrous ethyl ether (1.5 L) at 10° C. Vacuum filtration of the mixture followed by washing the white crystals with ethyl ether and drying in a vacuum oven at 5° C. for 2 hrs. gives 1140 g of the desired product.

Synthesis of 7- methylpentadecene-1-ol

Into a dried 5 L, 3 neck round bottom flask fitted with mechanical stirring, nitrogen inlet, dropping funnel, thermometer and nitrogen outlet is added 80 g of 60% sodium hydride (2.0 mol) in mineral oil. The mineral oil is removed by washing with hexanes. Anhydrous dimethyl sulfoxide (500 ml) is added to the flask and heated to 70° C. until evolution of hydrogen stops. The reaction mixture is cooled to room temperature followed by addition of 1 L of anhydrous tetrahydrofuran. (6-hydroxyhexyl) triphenylphosphonium bromide (443.4 g, 1 mol) is slurried with warm anhydrous dimethyl sulfoxide (50° C., 500 ml) and slowly added to the reaction mixture thru the dropping funnel while keeping the reaction at 25–30° C. The reaction is stirred for 30 minutes at room temperature at which time 2-decanone (171.9 g, 1.1 mol) is slowly added thru a dropping funnel. Reaction is slightly exothermic and cooling is needed to maintain 25–30° C. Mixture is stirred for 18 hrs. and then poured into a separatory funnel containing 600 ml of purified water and 300 ml of hexanes. After shaking the oil phase (top) is allowed to separate out and the water phase is removed. The extractions of the oil phase are continued using water until both phases are clear. The organic phase is collected, vacuum distilled and purified by liquid chromatography (90:10 hexanes:ethyl acetate, silica gel stationary phase) to obtain a clear, oily product (119.1 g).

Hydrogenation of 7- methylpentadecene-1-ol

Into a 3 L rocking autoclave glass liner (Autoclave Engineers) is added 7-Methylpentadecene-1-ol (122 g, 0.508 mol), methanol (300 ml) and platinum on carbon (10% by weight, 40 g). The mixture is hydrogenated at 180° C. under 1200 psig of hydrogen for 13 hrs., cooled and vacuum filtered thru Celite 545 with washing of Celite 545 with methylene chloride. The organic mixture is still dark from platinum catalyst so the filtration procedure is repeated with concentration on a rotary evaporator; dilution is carried out with methylene chloride (500 ml) and magnesium sulfate is added to dry product. Vacuum filter thru Celite 545 and concentrate filtrate on a rotary evaporator to obtain a clear oil (119 g).

Alkoxylation of 7-methylpentadecanol

Into a dried 1 L 3 neck round bottom flask fitted with a nitrogen inlet, mechanical stirrer, and a y-tube fitted with a thermometer and a gas outlet is added the alcohol from the preceeding step. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to five equivalents of ethylene oxide) has been added, nitrogen is swept through the apparatus for 20–30 minutes as the sample is allowed to cool. The desired 7-methylpentadecyl ethoxylate (average of 5 ethoxylates per molecule) product is then collected.

Sulfation of 7-methylpentadecyl ethoxylate (E5)

Into a dried 1 L 3 neck round bottom flask fitted with a nitrogen inlet, dropping funnel, thermometer, mechanical stirring and nitrogen outlet is added chloroform and 7-methylpentadecyl ethoxylate (E5) from the preceeding step. Chlorosulfonic acid is slowly added to the stirred mixture while maintaining 25–30° C. temperature with a ice bath. Once HCl evolution has stopped slowly add sodium methoxide (25% in methanol) while keeping temperature at 25–30° C. until a aliquot at 5% concentration in water maintains a pH of 10.5. To the mixture is added methanol and 1-butanol. Vacuum filter off the inorganic salt precipitate and remove methanol from the filtrate on a rotary evaporator. Cool to room temperature, add ethyl ether and let stand for 1 hour. The precipitate is collected by vacuum filtration to provide the desired 7-methylpentadecyl ethoxylate (average of 5 ethoxylates per molecule) sulfate, sodium salt, product.

EXAMPLE III

Synthesis of Sodium 7-methylheptadecyl ethoxylated (E1.5) and Sulfate

Synthesis of (6-Hydroxyhexyl) Triphenylphosphonium Bromide

Into a 4 L, 3 neck round bottom flask fitted with nitrogen inlet, condenser, thermometer, mechanical stirring and nitrogen outlet is added 6-bromo-1-hexanol (500 g, 2.76 mol), triphenylphosphine (768 g, 2.9 mol) and acetonitrile (1800 ml) under nitrogen. The reaction mixture is heated to reflux for 72 hrs. The reaction mixture is cooled to room temperature and transferred into a 5 L beaker. The product is recrystallized from anhydrous ethyl ether (1.5 L) at 10° C. Vacuum filtration of the mixture followed by washing the white crystals with ethyl ether and drying in a vacuum oven at 50° C. for 2 hrs. gives 1140 g of the desired product.

Synthesis of 7- methylheptadecene-1-ol

Into a dried 5 L, 3 neck round bottom flask fitted with mechanical stirring, nitrogen inlet, dropping funnel, thermometer and nitrogen outlet is added 80 g of 60% sodium hydride (2.0 mol) in mineral oil. The mineral oil is removed by washing with hexanes. Anhydrous dimethyl sulfoxide (500 ml) is added to the flask and heated to 70° C. until evolution of hydrogen stops. The reaction mixture is cooled to room temperature followed by addition of 1 L of anhydrous tetrahydrofuran. (6-hydroxyhexyl) triphenylphosphonium bromide (443.4 g, 1 mol) is slurried with warm anhydrous dimethyl sulfoxide (50° C., 500 ml) and slowly added to the reaction mixture thru the dropping funnel while keeping the reaction at 25–30° C. The reaction is stirred for 30 minutes at room temperature at which time 2-dodecanone (184.3 g, 1.1 mol) is slowly added thru a dropping funnel. Reaction is slightly exothermic and cooling is needed to maintain 25–30° C. Mixture is stirred for 18 hrs. and then poured into a separatory funnel containing 600 ml of purified water and 300 ml of hexanes. After shaking the oil phase (top) is allowed to separate out and the water phase is removed which is cloudy. The extractions are continued using water until the water phase and the organic phase become clear. The organic phase is collected and purified by liquid chromatography (mobile phase-hexanes, stationary phase-silica gel) to obtain a clear, oily product (116 g). HNMR of the final product (in deuterium oxide) indicates a $CH_2$—$OSO_3^-$ triplet at the 3.8 ppm resonance, $CH_2$—$CH_2$—$OSO_3^-$ multiplet at the 1.5 ppm resonance, $CH_2$ of the alkyl chain at the 0.9–1.3 ppm resonance and $CH$—$CH_3$ branch point overlapping the R—$CH_2CH_3$ terminal methyl group at the 0.8 ppm resonance.

Hydrogenation of 7- methylheptadecene-1-ol

Into a 3 L rocking autoclave glass liner (Autoclave Engineers) is added 7-Methylheptadecene-1-ol (116 g, 0.433 mol), methanol (300 ml) and platinum on carbon (10% by weight, 40 g). The mixture is hydrogenated at 180° C. under 1200 psig of hydrogen for 13 hrs., cooled and vacuum filtered thru Celite 545 with washing of Celite 545 with methylene chloride. Vacuum filter thru Celite 545 and concentrate filtrate on a rotary evaporator to obtain a clear oil (108 g).

Alkoxylation of 7-methylpentadecanol

Into a dried 1 L 3 neck round bottom flask fitted with a nitrogen inlet, mechanical stirrer, and a y-tube fitted with a thermometer and a gas outlet is added the alcohol from the preceeding step. For purposes of removing trace amounts of moisture, the alcohol is sparged with nitrogen for about 30 minutes at 80–100° C. Continuing with a nitrogen sweep, sodium metal is added as the catalyst and allowed to melt with stirring at 120–140° C. With vigorous stirring, ethylene oxide gas is added in 140 minutes while keeping the reaction temperature at 120–140° C. After the correct weight (equal to 1.5 equivalents of ethylene oxide) has been added, nitrogen is swept through the apparatus for 20–30 minutes as the sample is allowed to cool. The desired 7-methylheptadecyl ethoxylate (average of 1.5 ethoxylates per molecule) product is then collected.

Sulfation of 7-methylheptadecyl ethoxylate (E1.5)

Into a dried 1 L 3 neck round bottom flask fitted with a nitrogen inlet, dropping funnel, thermometer, mechanical stirring and nitrogen outlet is added chloroform and 7-methylheptadecyl ethoxylate (E1.5) from the preceeding step. Chlorosulfonic acid is slowly added to the stirred mixture while maintaining 25–30° C. temperature with a ice bath. Once HCl evolution has stopped slowly add sodium methoxide (25% in methanol) while keeping temperature at 25–30° C. until a aliquot at 5% concentration in water maintains a pH of 10.5. To the mixture is added hot methanol (45° C.) to dissolve the branched sulfate followed immediately by vacuum filtration to remove the inorganic salt precipitate and repeated a second time. The filtrate is then cooled to 5° C. at which time ethyl ether is added and let stand for 1 hour. The precipitate is collected by vacuum filtration to provide the desired 7-methylheptadecyl ethoxylate (average of 1.5 ethoxylates per molecule) sulfate, sodium salt, product.

EXAMPLE IV

The following Shell Research experimental test alcohol samples are ethoxylated (average ethoxylation of 2.5) and then sulfated by the following procedure.

| $^{13}$C-NMR Results For Branched Alcohols Prepared | | | |
|---|---|---|---|
| Total Number of Carbons | 16 | 17 | 18 |
| Avg. Number of Branches per Molecule | 2.0 | 1.7 | 2.1 |
| Average Branch Position Relative To Hydroxyl Carbon | | | |
| % at C4 and higher | 56% | 55% | 52% |
| % at C3 | 26% | 21% | 25% |
| % at C2 | 18% | 24% | 23% |
| Type of Branching | | | |
| % propyl and higher | 31% | 35% | 30% |
| % ethyl | 12% | 10% | 12% |
| % methyl | 57% | 55% | 58% |

Into a dried 250 ml 3 neck round bottom flask fitted with a nitrogen inlet, mechanical stirrer, and a y-tube fitted with a thermometer and a gas outlet is added the C16 alcohol (48.4 g, 0.2 mol) above. For purposes of removing trace amounts of moisture, the alcohol is sparged with nitrogen for about 30 minutes at 80–100° C. Continuing with a nitrogen sweep, sodium metal (0.23 g, 0.01 mol) is added as the catalyst and allowed to melt with stirring at 120–140° C. With vigorous stirring, ethylene oxide gas (22 g, 0.5 mol) is added in 140 minutes while keeping the reaction temperature at 120–140° C. After the correct weight of ethylene oxide (average 2.5 ethoxylates per molecule) has been added, nitrogen is swept through the apparatus for 20–30 minutes as the sample is allowed to cool. The gold liquid product (69 g, 0.196 mol) is bottled under nitrogen.

Sulfation of this C16 ethoxylate utilizes the following procedure. Into a dried 500 ml 3 neckround bottom flask fitted with a gas inlet, dropping funnel, mechanical stirrer, and a y-tube fitted with a thermometer and a gas outlet is added the C16 ethoxylate from the previous step (63.4 g, 0.18 mol) and diethyl ether (75 ml). Chlorosulfonic acid (22.1 g, 0.19 mol) is added slowly to the stirred mixture while maintaining a reaction temperature of 5–15° C. with an ice water bath. After the chlorosulfonic acid is added a slow nitrogen sweep and a vacuum (10–15 inches Hg) is begun to remove HCl. Also the reaction is warmed to 30–40° C. with the addition of a warm water bath. After about 45 minutes the vacuum is increased to 25–30 inches Hg and maintained for an additional 45 minutes. The acidic reaction mixture is slowly poured into a vigorously stirred beaker of 25% sodium methoxide (43.2 g, 0.2 mol) and methanol (200 ml) that is cooled in an ice water bath. After pH>12 is confirmed the solution is allowed to stir about 15 minutes then poured into a glass dish. Most of the solvent is allowed to evaporate overnight in the fume hood. The next morning the dish is transferred to a vacuum drying oven. The sample is allowed to dry all day and overnight at 40–60° C. with 25–30 inches Hg vacuum. Yellow tacky solid (80.9 g; 93% active) C16 ethoxylated (E2.5) sulfate, sodium salt, product is collected.

EXAMPLE V

Preparation of sodium 7-methylhexadecyl sulfate

Sulfation of 7-methylhexadecanol

Into a dried 1 L 3 neck round bottom flask fitted with a nitrogen inlet, dropping funnel, thermometer, mechanical stirring and nitrogen outlet is added chloroform (300 ml) and 7-methylhexadecanol (124 g, 0.484 mol), prepared as an intermediate in Example I. Chlorosulfonic acid (60 g, 0.509 mol) is slowly added to the stirred mixture while maintaining 25–30° C. temperature with a ice bath. Once HCl evolution has stopped (1 hr.) slowly add sodium methoxide (25% in methanol) while keeping temperature at 25–30° C. until an aliquot at 5% concentration in water maintains a pH of 10.5. To the mixture is added hot ethanol (55° C., 2 L). The mixture is vacuum filtered immediately. The filtrate is concentrated to a slurry on a rotary evaporator, cooled and then poured into 2 L of ethyl ether. The mixture is chilled to 5° C., at which point crystallization occurs, and vacuum filtered. The crystals are dried in a vacuum oven at 50 C. for 3 hrs. to obtain a white solid (136 g, 92% active by cat $SO_3$ titration).

EXAMPLE VI

Synthesis of sodium 7-methylpentadecyl sulfate

Sulfation of 7-methylpentadecanol

Into a dried 1 L 3 neck round bottom flask fitted with a nitrogen inlet, dropping funnel, thermometer, mechanical stirring and nitrogen outlet is added chloroform (300 ml) and 7-methylpentadecanol (119 g, 0.496 mol), prepared as an intermediate in Example II. Chlorosulfonic acid (61.3 g, 0.52 mol) is slowly added to the stirred mixture while maintaining 25–30° C. temperature with an ice bath. Once HCl evolution has stopped (1 hr.) slowly add sodium methoxide (25% in methanol) while keeping temperature at 25–30° C. until a aliquot at 5% concentration in water maintains a pH of 10.5. To the mixture is added methanol (1 L) and 300 ml of 1-butanol. Vacuum filter off the inorganic salt precipitate and remove methanol from the filtrate on a rotary evaporator. Cool to room temperature, add 1 L of ethyl ether and let stand for 1 hour. The precipitate is collected by vacuum filtration. The product is dried in a vacuum oven at 50 C. for 3 hrs. to obtain a white solid (82 g, 90% active by cat $SO_3$ titration).

EXAMPLE VII

Synthesis of sodium 7-methylheptadecyl sulfate

Sulfation of 7-methylheptadecanol

Into a dried 1 L 3 neck round bottom flask fitted with a nitrogen inlet, dropping funnel, thermometer, mechanical stirring and nitrogen outlet is added chloroform (300 ml) and 7-Methylheptadecanol (102 g, 0.378 mol), prepared as an intermediate in Example III. Chlorosulfonic acid (46.7 g, 0.40 mol) is slowly added to the stirred mixture while maintaining 25–30° C. temperature with a ice bath. Once HCl evolution has stopped (1 hr.) slowly add sodium methoxide (25% in methanol) while keeping temperature at 25–30° C. until an aliquot at 5% concentration in water maintains a pH of 10.5. To the mixture is added hot methanol (45° C.,1 L) to dissolve the branched sulfate followed immediately by vacuum filtration to remove the inorganic salt precipitate and repeated a second time. The filtrate is then cooled to 5° C. at which time 1 L of ethyl ether is added and let stand for 1 hour. The precipitate is collected by vacuum filtration. The product is dried in a vacuum oven at 50 C. for 3 hrs. to obtain a white solid (89 g, 88% active by cat $SO_3$ titration). HNMR of the final product (in deuterium oxide) indicates a $CH_2$—$OSO_3^-$ triplet at the 3.8 ppm resonance, $CH_2$—$CH_2$—$OSO_3^-$ multiplet at the 1.5 ppm resonance, $\overline{CH_2}$ of the alkyl chain at the 0.9–1.3 ppm resonance and $\overline{CH}$—$CH_3$ branch point overlapping the R—$CH_2CH_3$ terminal methyl group at the 0.8 ppm resonance. Mass spectrometry data shows a molecular ion peak with a mass of 349.1 corresponding to the 7-methylheptadecyl sulfate ion. Also shown is the methyl branch at the 7 position due to the loss of 29 mass units at that position.

The following two analytical methods for characterizing branching in the present invention surfactant compositions are useful:

1) Separation and Identification of Components in Fatty Alcohols (prior to alkoxylation or after hydrolysis of alcohol sulfate for analytical purposes). The position and length of branching found in the precursor fatty alcohol materials is determined by GC/MS techniques [see: D. J. Harvey, Biomed, Environ. Mass Spectrom (1989). 18(9), 719–23; D. J. Harvey, J. M. Tiffany, J. Chromatogr. (1984), 301(1), 173–87; K. A. Karlsson, B. E. Samuelsson, G. O. Steen, Chem. Phys. Lipids (1973), 11(1), 17–38].

2) Identification of Separated Fatty Alcohol Alkoxy Sulfate Components by MS/MS. The position and length of branching is also determinable by Ion Spray-MS/MS or FAB-MS/MS techniques on previously isolated fatty alcohol sulfate components.

The average total carbon atoms of the branched primary alkyl surfactants herein can be calculated from the hydroxyl value of the precursor fatty alcohol mix or from the hydroxyl value of the alcohols recovered by extraction after hydrolysis of the alcohol sulfate mix according to common procedures, such as outlined in "Bailey's Industrial Oil and Fat Products", Volume 2, Fourth Edition, edited by Daniel Swern, pp. 440–441.

Co-surfactants

The surfactant system of the liquid detergent compositions according to the present invention further comprise additional surfactants, herein also referred to as co-surfactants, preferably selected from: anionic surfactants, preferably selected from the group of alkyl alkoxylated sulfates, alkyl sulfates, allyl disulfates, and/or linear alkyl benzenesulfonate surfactants; cationic surfactants, preferably selected from quaternary ammonium surfactants; nonionic surfactants, preferably alkyl ethoxylates, alkyl polyglucosides, polyhydroxy fatty acid amides, and/or amine or amine oxide surfactants; amphoteric surfactants, preferably selected from betaines and/or polycarboxylates (for example polyglycinates); and zwiterionic surfactants.

A wide range of these co-surfactants can be used in the cleaning compositions of the present invention. A typical listing of anionic, nonionic, ampholytic and zwitterionic classes, and species of these co-surfactants, is given in U.S. Pat. No. 3,664,961 issued to Norris on May 23, 1972. Amphoteric surfactants are also described in detail in "Amphoteric Surfactants, Second Edition", E. G. Lomax, Editor (published 1996, by Marcel Dekker, Inc.)

The laundry detergent compositions of the present invention typically comprise from about 0.1% to about 35%, preferably from about 0.5% to about 15%, by weight of co-surfactants. Selected co-surfactants are further identified as follows.

(1) Anionic Co-surfactants

Nonlimiting examples of anionic co-surfactants useful herein, typically at levels from about 0.1% to about 50%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^- M^+) CH_3$ and $CH_3 (CH_2)_y(CHOSO_3^-M^+) CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alpha-sulfonated fatty acid esters, the $C_{10-C18}$ sulfated alkyl polyglycosides, the $C_{10}$–$C_{18}$ alkyl alkoxy sulfates ("$AE_xS$"; especially EO 1–7 ethoxy sulfates), and $C_{10}$–$C_{18}$ alkyl alkoxy carboxylates (especially the EO 1–5 ethoxycarboxylates). The $C_{12}$–$C_{18}$ betaines and sulfobetaines ("sultaines"), $C_{10}$–$C_{18}$ amine oxides, and the like, can also be included in the overall compositions. $C_{10}$–$C_{20}$ conventional soaps may also be used. If high sudsing is desired, the branched-chain $C_{10}$–$C_{16}$ soaps may be used. Other conventional useful anionic co-surfactants are listed in standard texts.

The alkyl alkoxylated sulfate surfactants useful herein are preferably water soluble salts or acids of the formula $RO(A)_m SO_3M$ wherein R is an unsubstituted $C_{10}$–$C_{24}$ alkyl or hydroxyalkyl group having a $C_{10}$–$C_{24}$ alkyl component, preferably a $C_{12}$–$C_{18}$ alkyl or hydroxyalkyl, more preferably $C_{12}$–$C_{15}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include ethanol-, triethanol-, methyl-, dimethyl, trimethyl-ammonium cations and quaternary ammonium cations such as tetramethyl-ammonium and dimethyl piperidinium cations and those derived from alkylamines such as ethylamine, diethylamine, triethylamine, mixtures thereof, and the like. Exemplary surfactants are $C_{12}$–$C_{15}$ alkyl polyethoxylate (1.0) sulfate ($C_{12}$–$C_{15}$E(1.0) M), $C_{12}$–$C_{15}$ alkyl polyethoxylate (2.25) sulfate ($C_{12}$–$C_{15}$E (2.25)M), $C_{12}$–$C_{15}$ alkyl polyethoxylate (3.0) sulfate ($C_{12-C15}$E(3.0)M), and $C_{12}$–$C_{15}$ alkyl polyethoxylate (4.0) sulfate ($C_{12}$–$C_{15}$E(4.0)M), wherein M is conveniently selected from sodium and potassium.

The alkyl sulfate surfactants useful herein are preferably water soluble salts or acids of the formula $ROSO_3M$ wherein R preferably is a $C_{10}$–$C_{24}$ hydrocarbyl, preferably an alkyl or hydroxyalkyl having a $C_{10}$–$C_{18}$ alkyl component, more preferably a $C_{12}$–$C_{15}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperidinium cations and quaternary ammonium cations derived from alkylamines such as ethylamine, diethylamine, triethylamine, and mixtures thereof, and the like).

Other suitable anionic surfactants that can be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

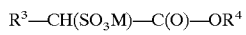

$R^3$—CH($SO_3$M)—C(O)—$OR^4$ wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other anionic co-surfactants useful for detersive purposes can also be included in the laundry detergent compositions of the present invention. These can include salts (including, for example, sodium, potassium, ammonium, and substituted ammonium salts such as mono-, di- and triethanolamine salts) of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as descrued in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleoyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), sulfates of alkylpolysaccharides such as the sulfates of alkylpolyglucoside (the nonionic nonsulfated compounds being described below), and alkyl polyethoxy carboxylates such as those of the formula $RO(CH_2CH_2O)_k$—$CH_2COO$—M+ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

A preferred disulfate surfactant has the formula

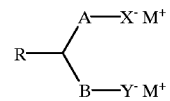

where R is an alkyl, substituted alkyl, alkenyl, aryl, alkaryl, ether, ester, amine or amide group of chain length $C_1$ to $C_{28}$, preferably $C_3$ to $C_{24}$, most preferably $C_8$ to $C_{20}$, or hydrogen; A and B are independently selected from alkyl, substituted alkyl, and alkenyl groups of chain length $C_1$ to $C_{28}$, preferably $C_1$ to $C_5$, most preferably $C_1$ or $C_2$, or a covalent bond, and A and B in total contain at least 2 atoms; A, B, and R in total contain from 4 to about 31 carbon atoms; X and Y are anionic groups selected from the group consisting of sulfate and sulfonate, provided that at least one of X or Y is a sulfate group; and M is a cationic moiety, preferably a substituted or unsubstituted ammonium ion, or an alkali or alkaline earth metal ion.

The most preferred disulfate surfactant has the formula as above where R is an alkyl group of chain length from $C_{10}$ to $C_{18}$, A and B are independently $C_1$ or $C_2$, both X and Y are sulfate groups, and M is a potassium, ammonium, or a sodium ion.

The disulfate surfactant is typically present at levels of incorporation of from about 0.1% to about 50%, preferably from about 0.1% to about 35%, most preferably from about 0.5% to about 15% by weight of the detergent composition.

Preferred disulfate surfactant herein include:

(a) 1,3 disulfate compounds, preferably 1,3 C7–C23 (i.e., the total number of carbons in the molecule) straight or branched chain alkyl or alkenyl disulfates, more preferably having the formula:

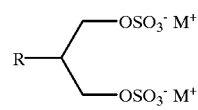

wherein R is a straight or branched chain alkyl or alkenyl group of chain length from about $C_4$ to about $C_{18}$;

(b) 1,4 disulfate compounds, preferably 1,4 C8–C22 straight or branched chain alkyl or alkenyl disulfates, more preferably having the formula:

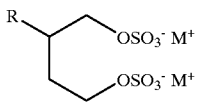

wherein R is a straight or branched chain alkyl or alkenyl group of chain length from about $C_4$ to about C 18; preferred R are selected from octanyl, nonanyl, decyl, dodecyl, tetradecyl, hexadecyl, octadecyl, and mixtures thereof; and (c) 1,5 disulfate compounds, preferably 1,5 C9–C23 straight or branched chain alkyl or alkenyl disulfates, more preferably having the formula:

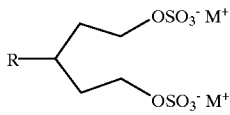

wherein R is a straight or branched chain alkyl or alkenyl group of chain length from about $C_4$ to about $C_{18}$.

Known syntheses of certain disulfated surfactants, in general, use an alkyl or alkenyl succinic anhydride as the principal starting material. This is initially subjected to a reduction step from which a diol is obtained. Subsequently the diol is subjected to a sulfation step to give the disulfated product. As an example, U.S. Pat. No. 3,634,269 describes 2-alkyl or alkenyl-1,4-butanediol disulfates prepared by the reduction of alkenyl succinic anhydrides with lithium aluminium hydride to produce either alkenyl or alkyl diols which are then sulfated. In addition, U.S. Pat. No. 3,959,334 and U.S. Pat. No. 4,000,081 describe 2-hydrocarbyl-1,4-butanediol disulfates also prepared using a method involving the reduction of alkenyl succinic anhydrides with lithium aluminium hydride to produce either alkenyl or alkyl diols which are then sulfated.

See also U.S. Pat. No. 3,832,408 and U.S. Pat. No. 3,860,625 which describe 2-alkyl or alkenyl-1,4-butanediol ethoxylate disulfates prepared by the reduction of alkenyl succinic anhydrides with lithium aluminium hydride to produce either alkenyl or alkyl diols which are then ethoxylated prior to sulfation.

These compounds may also be made by a method involving synthesis of the disulfate surfactant from a substituted cyclic anhydride having one or more carbon chain substituents having in total at least 5 carbon atoms comprising the following steps:

(i) reduction of said substituted cyclic anhydride to form a diol; and (ii) sulfation of said diol to form a disulfate wherein said reduction step comprises hydrogenation under pressure in the presence of a transition metal-containing hydrogenation catalyst.

When included therein, the laundry detergent compositions of the present invention typically comprise from about 0.1% to about 50%, preferably from about 1% to about 40% by weight of an anionic surfactant.

(2) Nonionic Co-surfactants

Nonlimiting examples of nonionic co-surfactants usefully herein typically at to levels from about 0.1% to about 50%, by weight include the alkoxylated alcohols (AE's) and alkyl phenols, polyhydroxy fatty acid amides (PFAA's), alkyl polyglycosides (APG's), $C_{10}$–$C_{18}$ glycerol ethers, and the like.

More specifically, the condensation products of primary and secondary aliphatic alcohols with from about 1 to about 25 moles of ethylene oxide (AE) are suitable for use as the nonionic surfactant in the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 1 to about 10 moles, preferably 2 to 7, most preferably 2 to 5, of ethylene oxide per mole of alcohol. Especially preferred nonionic surfactants of this type are the $C_9$–$C_{15}$ primary alcohol ethoxylates containing 3–12 moles of ethylene oxide per mole of alcohol, particularly the $C_{12}$–$C_{15}$ primary alcohols containing 5–10 moles of ethylene oxide per mole of alcohol.

Examples of commercially available nonionic surfactants of this type include: Tergitol™ 15-S-9 (the condensation product of $C_{11}$–$C_{15}$ linear alcohol with 9 moles ethylene oxide) and Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45–9 (the condensation product of $C_{14}$–$C_{15}$ linear alcohol with 9 moles of ethylene oxide), Neodol™ 23–3 (the condensation product of $C_{12}$–$C_{13}$ linear alcohol with 3 moles of ethylene oxide), Neodol™ 45–7 (the condensation product of $C_{14}$–$C_{15}$ linear alcohol with 7 moles of ethylene oxide) and Neodol™ 45–5 (the condensation product of $C_{14}$–$C_{15}$ linear alcohol with 5 moles of ethylene oxide) marketed by Shell Chemical Company; Kyro™ EOB (the condensation product of $C_{13}$–$C_{15}$ alcohol with 9 moles ethylene oxide), marketed by The Procter & Gamble Company; and Genapol LA O3O or O5O (the condensation product of $C_{12}$–$C_{14}$ alcohol with 3 or 5 moles of ethylene oxide) marketed by Hoechst. The preferred range of HLB in these AE nonionic surfactants is from 8–17 and most preferred from 8–14. Condensates with propylene oxide and butylene oxides may also be used.

Another class of preferred nonionic co-surfactants for use herein are the polyhydroxy fatty acid amide surfactants of the formula

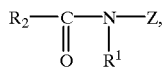

wherein $R^1$ is H, or $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof Preferably, $R^1$ is methyl, $R^2$ is a straight $C_{11-15}$ alkyl or $C_{15-17}$ alkyl or alkenyl chain such as coconut alkyl or mixtures thereof, and Z is derived from a reducing sugar such as glucose, fructose, maltose, lactose, in a reductive amination reaction. Typical examples include the $C_{12}$–$C_{18}$ and $C_{12}$–$C_{14}$ N-methylglucamides. See U.S. Pat. Nos. 5,194, 639 and 5,298,636. N-alkoxy polyhydroxy fatty acid amides can also be used; see U.S. Pat. No. 5,489,393.

Also useful as a nonionic co-surfactant in the present invention are the alkylpolysaccharides such as those disclosed in U.S. Pat. No. 4,565,647, Llenado, issued Jan. 21, 1986, having a hydrophobic group containing from about 6 to about 30 carbon atoms, preferably from about 10 to about 16 carbon atoms, and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6- positions on the preceding saccharide units.

Preferred alkylpolyglycosides have the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position. Compounds of this type and their use in detergent are disclosed in EP-B 0 070 077, 0 075 996 and 0 094 118.

Polyethylene, polypropylene, and polybutylene oxide condensates of alkyl phenols are also suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-1 14, X-100 and X-102, all marketed by the Rohm & Haas Company. These surfactants are commonly referred to as alkylphenol alkoxylates (e.g., alkyl phenol ethoxylates).

The condensation products of ethylene oxide with a hydrophobic base formed by the condensation of propylene oxide with propylene glycol are also suitable for use as the additional nonionic surfactant in the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 1,000. Examples of this type of nonionic surfactant include certain of the commercially available Tetronic™ compounds, marketed by BASF.

Also preferred nonionics are amine oxide surfactants. The compositions of the present invention may comprise amine oxide in accordance with the general formula I:

$$R^1(EO)_x(PO)_y(BO)_zN(O)(CH_2R')_2 \cdot qH_2O \qquad (I).$$

In general, it can be seen that the structure (I) provides one long-chain moiety $R^1(EO)_x(PO)_y(BO)_z$ and two short chain moieties, $CH_2R'$. $R'$ is preferably selected from hydrogen, methyl and —$CH_2OH$. In general $R^1$ is a primary or branched hydrocarbyl moiety which can be saturated or unsaturated, preferably, $R^1$ is a primary alkyl moiety. When x+y+z=0, $R^1$ is a hydrocarbyl moiety having chainlength of from about 8 to about 18. When x+y+z is different from 0, $R^1$ may be somewhat longer, having a chainlength in the range $C_{12}$–$C_{24}$. The general formula also encompasses amine oxides wherein x+y+z=0, $R_1=C_8$–$C_{18}$, $R'=H$ and q=0–2, preferably 2. These amine oxides are illustrated by $C_{12-14}$ alkyldimethyl amine oxide, hexadecyl dimethylamine oxide, octadecylamine oxide and their hydrates, especially the dihydrates as disclosed in U.S. Pat. Nos. 5,075,501 and 5,071,594, incorporated herein by reference.

The invention also encompasses amine oxides wherein x+y+z is different from zero, specifically x+y+z is from about 1 to about 10, $R^1$ is a primary alkyl group containing 8 to about 24 carbons, preferably from about 12 to about 16 carbon atoms; in these embodiments y+z is preferably 0 and x is preferably from about 1 to about 6, more preferably from about 2 to about 4; EO represents ethyleneoxy; PO represents propyleneoxy; and BO represents butyleneoxy. Such amine oxides can be prepared by conventional synthetic methods, e.g., by the reaction of alkylethoxysulfates with dimethylamine followed by oxidation of the ethoxylated amine with hydrogen peroxide.

Highly preferred amine oxides herein are solutions at ambient temperature. Amine oxides suitable for use herein are made commercially by a number of suppliers, including Akzo Chemie, Ethyl Corp., and Procter & Gamble. See McCutcheon's compilation and Kirk-Othmer review article for alternate amine oxide manufacturers.

Whereas in certain of the preferred embodiments R'0 is H, there is some latitude with respect to having R' slightly larger than H. Specifically, the invention further encompasses embodiments wherein R' is $CH_2OH$, such as hexadecylbis(2-hydroxyethyl)amine oxide, tallowbis(2-hydroxyethyl)amine oxide, stearylbis(2-hydroxyethyl) amine oxide and oleylbis(2-hydroxyethyl)amine oxide, dodecyldimethylamine oxide dihydrate.

Preferred amines for use herein include amines according to the formula:

$$R_1-X-(CH_2)_n-N(R_3)(R_4)$$

wherein $R_1$ is a $C_6$–$C_{12}$ alkyl group; n is from about 2 to about 4, X is a bridging group which is selected from NH, CONH, COO, or O or X can be absent; and $R_3$ and $R_4$ are individually selected from H, $C_1$–$C_4$ alkyl, or ($CH_2$—$CH_2$—$O(R_5)$) wherein $R_5$ is H or methyl.

These preferred amines include the following:

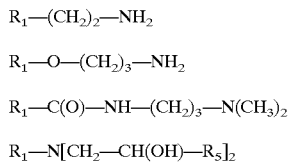

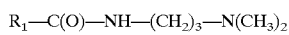

wherein $R_1$ is a $C_6-C_{12}$ alkyl group and $R_5$ is H or $CH_3$.

In a highly preferred embodiment, the amine is described by the formula:

$$R_1-C(O)-NH-(CH_2)_3-N(CH_3)_2$$

wherein $R_1$ is $C_8-C_{12}$ alkyl.

Particularly preferred amines include those selected from the group consisting of octyl amine, hexyl amine, decyl amine, dodecyl amine, $C_8-C_{12}$ bis(hydroxyethyl)amine, $C_8-C_{12}$ bis(hydroxyisopropyl)amine, and $C_8-C_{12}$ amidopropyl dimethyl amine, and mixtures.

(3) Cationic Co-surfactants:

Nonlimiting examples of cationic co-surfactants useful herein typically at levels from about 0.1% to about 50%, by weight include the choline ester-type quats and alkoxylated quaternary ammonium (AQA) surfactant compounds, and the like. Most preferred for aqueous liquid compositions herein are soluble cationic co-surfactants which do not readily hydrolyze in the product.

Cationic co-surfactants useful as a component of the surfactant system is a cationic choline ester-type quat surfactant which are preferably water dispersible compounds having surfactant properties and comprise at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529.

Cationic ester surfactants include those having the formula:

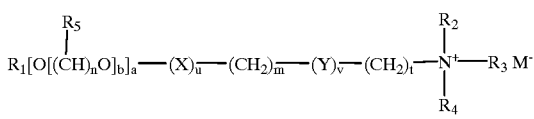

wherein $R_1$ is a $C_5-C_{31}$ linear or branched alkyl, alkenyl or alkaryl chain or $M^-.N^+(R_6R_7R_8)(CH_2)s$; X and Y, independently, are selected from the group consisting of COO, OCO, O, CO, OCOO, CONH, NHCO, OCONH and NHCOO wherein at least one of X or Y is a COO, OCO, OCOO, OCONH or NHCOO group; $R_2$, $R_3$, $R_4$, $R_6$, $R_7$ and $R_8$ are independently selected from the group consisting of alkyl, alkenyl, hydroxyalkyl, hydroxyalkenyl and alkaryl groups having from 1 to 4 carbon atoms; and $R_5$ is independently H or a $C_1-C_3$ alkyl group; wherein the values of m, n, s and t independently lie in the range of from 0 to 8, the value of b lies in the range from 0 to 20, and the values of a, u and v independently are either 0 or 1 with the proviso that at least one of u or v must be 1; and wherein M is a counter anion.

Preferably $R_2$, $R_3$ and $R_4$ are independently selected from $CH_3$ and —$CH_2CH_2OH$.

Preferably M is selected from the group consisting of halide, methyl sulfate, sulfate, and nitrate, more preferably methyl sulfate, chloride, bromide or iodide.

Preferred water dispersible cationic ester surfactants are the choline esters having the formula:

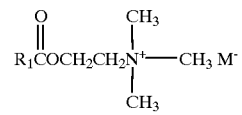

wherein $R_1$ is a $C_{11}-C_{19}$ linear or branched alkyl chain.

Particularly preferred choline esters of this type include the stearoyl choline ester quaternary methylammonium halides ($R^1=C_{17}$ alkyl), palmitoyl choline ester quaternary methylammonium halides ($R^1=C_{15}$ alkyl), myristoyl choline ester quaternary methylammonium halides ($R^1=C_{13}$ alkyl), lauroyl choline ester quaternary methylammonium halides ($R^1=C_{11}$ alkyl), cocoyl choline ester quaternary methylammonium halides ($R^1=C_{11}-C_{13}$ alkyl), tallowyl choline ester quaternary methylammonium halides ($R^1=C_{15}-C_{17}$ alkyl), and any mixtures thereof.

The particularly preferred choline esters, given above, may be prepared by the direct esterification of a fatty acid of the desired chain length with dimethylaminoethanol, in the presence of an acid catalyst. The reaction product is then quaternized with a methyl halide, preferably in the presence of a solvent such as ethanol, propylene glycol or preferably a fatty alcohol ethoxylate such as $C_{10}-C_{18}$ fatty alcohol ethoxylate having a degree of ethoxylation of from 3 to 50 ethoxy groups per mole forming the desired cationic material. They may also be prepared by the direct esterification of a long chain fatty acid of the desired chain length together with 2-haloethanol, in the presence of an acid catalyst material. The reaction product is then quaternized with trimethylamine, forming the desired cationic material.

Other suitable cationic ester surfactants have the structural formulas below, wherein d may be from 0 to 20.

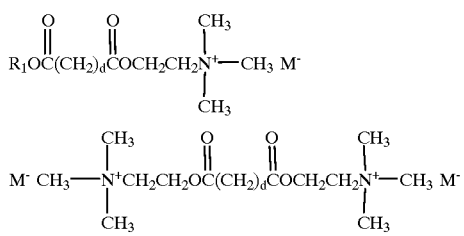

In a preferred aspect these cationic ester surfactant are hydrolysable under the conditions of a laundry wash method.

Cationic co-surfactants useful herein also include alkoxylated quaternary ammonium (AQA) surfactant compounds (referred to hereinafter as "AQA compounds") having the formula:

I

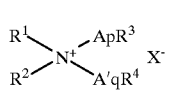

wherein $R^1$ is an alkyl or alkenyl moiety containing from about 8 to about 18 carbon atoms, preferably 10 to about 16 carbon atoms, most preferably from about 10 to about 14 carbon atoms; $R^2$ is an alkyl group containing from one to three carbon atoms, preferably methyl; $R^3$ and $R^4$ can vary independently and are selected from hydrogen (preferred), methyl and ethyl; $X^-$ is an anion such as chloride, bromide, methylsulfate, sulfate, or the like, sufficient to provide electrical neutrality. A and A' can vary independently and are each selected from $C_1$–$C_4$ alkoxy, especially ethoxy (i.e., —$CH_2CH_2O$—), propoxy, butoxy and mixed ethoxy/propoxy; p is from 0 to about 30, preferably 1 to about 4 and q is from 0 to about 30, preferably 1 to about 4, and most preferably to about 4; preferably both p and q are 1. See also: EP 2,084, published May 30, 1979, by The Procter & Gamble Company, which describes cationic co-surfactants of this type which are also useful herein.

The levels of the AQA surfactants used to prepare finished laundry detergent compositions typically range from about 0.1% to about 5%, preferably from about 0.45% to about 2.5%, by weight.

According to the foregoing, the following are nonlimiting, specific illustrations of AQA surfactants used herein. It is to be understood that the degree of alkoxylation noted herein for the AQA surfactants is reported as an average, following common practice for conventional ethoxylated nonionic surfactants. This is because the ethoxylation reactions typically yield mixtures of materials with differing degrees of ethoxylation. Thus, it is not uncommon to report total EO values other than as whole numbers, e.g., "EO2.5", "EO3.5", and the like.

| Designation | $R^1$ | $R^2$ | $ApR^3$ | $A'qR^4$ |
|---|---|---|---|---|
| AQA-1 (also referred to as Coco Methyl EO2) | $C_{12}$–$C_{14}$ | $CH_3$ | EO | EO |
| AQA-2 | $C_{12}$–$C_{16}$ | $CH_3$ | $(EO)_2$ | EO |
| AQA-3 (Coco Methyl EO4) | $C_{12}$–$C_{14}$ | $CH_3$ | $(EO)_2$ | $(EO)_2$ |
| AQA-4 | $C_{12}$ | $CH_3$ | EO | EO |
| AQA-5 | $C_{12}$–$C_{14}$ | $CH_3$ | $(EO)_2$ | $(EO)_3$ |
| AQA-6 | $C_{12}$–$C_{14}$ | $CH_3$ | $(EO)_2$ | $(EO)_3$ |
| AQA-7 | $C_8$–$C_{18}$ | $CH_3$ | $(EO)_3$ | $(EO)_2$ |
| AQA-8 | $C_{12}$–$C_{14}$ | $CH_3$ | $(EO)_4$ | $(EO)_4$ |
| AQA-9 | $C_{12}$–$C_{14}$ | $C_2H_5$ | $(EO)_3$ | $(EO)_3$ |
| AQA-10 | $C_{12}$–$C_{18}$ | $CH_7$ | $(EO)_3$ | $(EO)_4$ |
| AQA-11 | $C_{12}$–$C_{18}$ | $CH_3$ | (propoxy) | $(EO)_3$ |
| AQA-12 | $C_{10}$–$C_{18}$ | $C_2H_5$ | (iso-propoxy)$_2$ | $(EO)_3$ |
| AQA-13 | $C_{10}$–$C_{18}$ | $CH_3$ | $(EO/PO)_2$ | $(EO)_3$ |
| AQA-14 | $C_8$–$C_{18}$ | $CH_3$ | $(EO)_{15}$* | $(EO)_{15}$* |
| AQA-15 | $C_{10}$ | $CH_3$ | EO | EO |
| AQA-16 | $C_8$–$C_{12}$ | $CH_3$ | EO | EO |
| AQA-17 | $C_9$–$C_{11}$ | $CH_3$ | - EO 3.5 Avg. - | |
| AQA-18 | $C_{12}$ | $CH_3$ | - EO 3.5 Avg. - | |
| AQA-19 | $C_8$–$C_{14}$ | $CH_3$ | $(EO)_{10}$ | $(EO)_{10}$ |
| AQA-20 | $C_{10}$ | $C_2H_5$ | $(EO)_2$ | $(EO)_3$ |
| AQA-21 | $C_{12}$–$C_{14}$ | $C_2H_5$ | $(EO)_5$ | $(EO)_3$ |
| AQA-22 | $C_{12}$–$C_{18}$ | $C_3H_7$ | Bu | $(EO)_2$ |

*Ethoxy, optionally end-capped with methyl or ethyl.

The preferred bis-ethoxylated cationic surfactants herein are available under the trade name ETHOQUAD from Akzo Nobel Chemicals Company.

Highly preferred bis-AQA compounds for use herein are of the formula

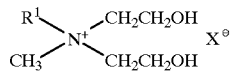

wherein $R^1$ is $C_{10}$–$C_{18}$ hydrocarbyl and mixtures thereof, preferably $C_{10}$, $C_{12}$, $C_{14}$ alkyl and mixtures thereof, and X is any convenient anion to provide charge balance, preferably chloride. With reference to the general AQA structure noted above, since in a preferred compound $R^1$ is derived from coconut ($C_{12}$–$C_{14}$ alkyl) fraction fatty acids, $R^2$ is methyl and $ApR^3$ and $A'qR^4$ are each monoethoxy, this preferred type of compound is referred to herein as "CocoMeEO2" or "AQA-1" in the above list.

Other preferred AQA compounds herein include compounds of the formula:

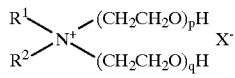

wherein $R^1$ is $C_{10}$–$C_{18}$ hydrocarbyl, preferably $C_{10}$–$C_{14}$ alkyl, independently p is 1 to about 3 and q is 1 to about 3, $R^2$ is $C_1$–$C_3$ alkyl, preferably methyl, and X is an anion, especially chloride.

Other compounds of the foregoing type include those wherein the ethoxy ($CH_2CH_2O$) units (EO) are replaced by butoxy (Bu), isopropoxy [$CH(CH_3)CH_2O$] and [$CH_2CH(CH_3O)$] units (i-Pr) or n-propoxy units (Pr), or mixtures of EO and/or Pr and/or i-Pr units.

Solvents

Liquid cleaning compositions further comprise water and/or other solvents. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from about 1% to about 99.7%, preferably from about 5% to about 90%, and most typically from about 10% to about 50% of solvents.

Heavy duty liquid detergent compositions herein, especially those designed for fabric laundering, may also comprise a non-aqueous carrier medium as described in more detail hereinafter.

Liquid Cleaning Composition Adjunct Ingredients

The heavy duty liquid detergent compositions according to the present invention preferably further comprise a builder system. Any conventional builder system or mixed builder system is suitable for use herein including aluminosilicate materials, silicates, polycarboxylates and fatty acids, materials such as ethylenediamine tetra-acetate, metal ion sequestrants such as aminopolyphosphonates, particularly ethylenediamine tetramethylene phosphonic acid and diethylene triamine pentamethylene phosphonic acid. Though less preferred for obvious environmental reasons, phosphate builders can also be used herein. Most preferred laundry detergent compositions according to the present invention comprise citrate/fatty acid mixed builder systems.

Suitable polycarboxylates builders for use herein include citric acid, preferably in the form of a water-soluble salt, derivatives of succinic acid of the formula R—$CH(COOH)CH_2(COOH)$ wherein R is $C_{10-20}$ alkyl or alkenyl, preferably $C_{12-16}$, or wherein R can be substituted with hydroxyl, sulfo sulfoxyl or sulfone substituents. Specific examples include lauryl succinate, myristyl succinate, palmityl succinate 2-dodecenylsuccinate, 2-tetradecenyl succinate. Succinate builders are preferably used in the form of their water-soluble salts, including sodium, potassium, ammonium and alkanolammonium salts.

Other suitable polycarboxylates are oxodisuccinates and mixtures of tartrate monosuccinic and tartrate disuccinic acid such as described in U.S. Pat. No. 4,663,071, as well as maleates.

Especially for the liquid execution herein, suitable fatty acid builders for use herein are saturated or unsaturated $C_{10-18}$ fatty acids, as well as the corresponding soaps. Preferred saturated species have from 12 to 16 carbon atoms in the alkyl chain. The preferred unsaturated fatty acid is oleic acid. Other preferred builder system for liquid compositions is based on dodecenyl succinic acid and citric acid.

Detergency builders are normally included in amounts of from 0.5% to 50% by weight of the composition preferably from 3% to 30% and most usually from 5% to 15% by weight.

Preferred detergent compositions of the present invention may further comprise one or more enzymes which provide cleaning performance and/or fabric care benefits. Said enzymes include enzymes selected from cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, β-glucanases, arabinosidases or mixtures thereof.

A preferred combination is a detergent composition having a cocktail of conventional applicable enzymes like protease, amylase, lipase, cutinase and/or cellulase in conjunction with the lipolytic enzyme variant D96 L at a level of from 50 LU to 8500 LU per liter wash solution.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, which discloses fungal cellulase produced from *Humicola insolens*. Suitable cellulases are also disclosed in GB-A-2.075.028; GB-A-2.095.275 and DE-OS-2.247.832.

Examples of such cellulases are cellulases produced by a strain of *Humicola insolens* (*Humicola grisea* var. *thermoidea*), particularly the Humicola strain DSM 1800. Other suitable cellulases are cellulases originated from *Humicola insolens* having a molecular weight of about 50 KDa, an isoelectric point of 5.5 and containing 415 amino acids. Especially suitable cellulases are the cellulases having color care benefits. Examples of such cellulases are cellulases described in European patent application No. 91202879.2, filed Nov. 6, 1991 (Novo).

Peroxidase enzymes are used in combination with oxygen sources, e.g. percarbonate, perborate, persulfate, hydrogen peroxide, etc. They are used for "solution bleaching", i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813 and in European Patent application EP No. 91202882.6, filed on Nov. 6, 1991.

Said cellulases and/or peroxidases are normally incorporated in the detergent composition at levels from 0.0001% to 2% of active enzyme by weight of the detergent composition.

Preferred commercially available protease enzymes include those sold under the tradenames Alcalase, Savinase, Primase, Durazymn, and Esperase by Novo Nordisk A/S (Denmark), those sold under the tradename Maxatase, Maxacal and Maxapem by Gist-Brocades, those sold by Genencor International, and those sold under the tradename Opticlean and Optimase by Solvay Enzymes. Also proteases described in our co-pending application U.S. Ser. No. 08/136,797 can be included in the detergent composition of the invention. Protease enzyme may be incorporated into the compositions in accordance with the invention at a level of from 0.0001% to 2% active enzyme by weight of the composition.

A preferred protease herein referred to as "Protease D" is a carbonyl hydrolase variant having an amino acid sequence not found in nature, which is derived from a precursor carbonyl hydrolase by substituting a different amino acid for the amino acid residue at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +204, +206, +210, +216, +217, +218, +222, +260, +265, and/or +274 according to the numbering of *Bacillus amyloliquefaciens* subtilisin, as described in WO 95/10615 published Apr. 20, 1995 by Genencor International.

Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Highly preferred enzymes that can be included in the detergent compositions of the present invention include lipases. It has been found that the cleaning performance on greasy soils is synergistically improved by using lipases. Suitable lipase enzymes include those produced by microorganisms of the Pseudomonas group, such as *Pseudomonas stutzeri* ATCC 19.154, as disclosed in British Patent 1,372, 034. Suitable lipases include those which show a positive immunological cross-reaction with the antibody of the lipase, produced by the microorganism *Pseudomonas fluorescens* IAM 1057. This lipase is available from Amano Pharmaceutical Co. Ltd., Nagoya, Japan, under the trade name Lipase P "Amano," hereinafter referred to as "Amano-P". Further suitable lipases are lipases such as M1 Lipase® and Lipomax® (Gist-Brocades). Highly preferred lipases are the D96 L lipolytic enzyme variant of the native lipase derived from *Humicola lanuginosa* as described in U.S. Ser. No. 08/341,826. Preferably the *Humicola lanuginosa* strain DSM 4106 is used. This enzyme is incorporated into the composition in accordance with the invention at a level of from 50 LU to 8500 LU per liter wash solution. Preferably the variant D96 L is present at a level of from 100 LU to 7500 LU per liter of wash solution. More preferably at a level of from 150 LU to 5000 LU per liter of wash solution.

By D96 L lipolytic enzyme variant is meant the lipase variant as described in patent application WO 92/05249 viz. wherein the native lipase ex *Humicola lanuginosa* aspartic acid (D) residue at position 96 is changed to Leucine (L). According to this nomenclature said substitution of aspartic acid to Leucine in position 96 is shown as: D96 L.

Also suitable are cutinases [EC 3.1.1.50] which can be considered as a special kind of lipase, namely lipases which do not require interfacial activation. Addition of cutinases to detergent compositions have been described in e.g. WO-A-88/09367 (Genencor).

The lipases and/or cutinases are normally incorporated in the detergent composition at levels from 0.0001% to 2% of active enzyme by weight of the detergent composition.

Amylases (& and/or β) can be included for removal of carbohydrate-based stains. Suitable amylases are Termamyl$^R$ (Novo Nordisk), Fungamyl$^R$ and BAN$^R$ (Novo Nordisk).

Certain preferred embodiments of the present compositions can make use of amylases having improved stability in detergents, especially improved oxidative stability as measured against a reference-point of TERMAMYL® in commercial use in 1993. These preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9–10; thermal stability, e.g., at common wash temperatures such as about 60° C.; or alkaline stability, e.g., at a pH from about 8 to about 11, measured versus the above-identified reference-point amylase. Stability can be measured using any of the art-disclosed technical tests. See, for example, references disclosed in WO 9402597. Stability-enhanced amylases can be obtained from Novo or from Genencor International. One class of highly preferred amylases herein have the commonality of being derived using site-directed mutagenesis from one or more of the *Bacillus amylases*, especially the *Bacillus α-amylases*, regardless of whether one, two or multiple amylase strains are the immediate precursors. Oxidative stability-enhanced amylases vs. the above-identified reference amylase are preferred for use, especially in bleaching, more preferably oxygen bleaching, as distinct from chlorine bleaching, detergent compositions herein. Such preferred amylases include (a) an amylase according to the hereinbefore incorporated WO 9402597, Novo, Feb. 3, 1994, as further illustrated by a mutant in which substitution is made, using alanine or threonine, preferably threonine, of the methionine residue located in position 197 of the *B. licheniformis* alpha-amylase, known as TERMAMYL®, or the homologous position variation of a similar parent amylase, such as *B. amyloliquefaciens, B. subtilis*, or *B. stearothermophilus*; (b) stability-enhanced amylases as described by Genencor International in a paper entitled "Oxidatively Resistant alpha-Amylases" presented at the 207th American Chemical Society National Meeting, Mar. 13–17 1994, by C. Mitchinson. Therein it was noted that bleaches in automatic dishwashing detergents inactivate alpha-amylases but that improved oxidative stability amylases have been made by Genencor from *B. licheniformis* NCIB8061. Methionine (Met) was identified as the most likely residue to be modified. Met was substituted, one at a time, in positions 8, 15, 197, 256, 304, 366 and 438 leading to specific mutants, particularly important being M197 L and M197T with the M197T variant being the most stable expressed variant. Stability was measured in CASCADE® and SUNLIGHT®; (c) particularly preferred amylases herein include amylase variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

The above-mentioned enzymes may be of any suitable origin, such as vegetable, animal, bacterial, fungal and yeast origin.

Said enzymes are normally incorporated in the detergent composition at levels from 0.0001% to 2% of active enzyme by weight of the detergent composition. Other suitable detergent ingredients that can be added are enzyme oxidation scavengers which are described in Copending European Patent application 92870018.6 filed on Jan. 31, 1992. Examples of such enzyme oxidation scavengers are ethoxylated tetraethylene polyamines.

Other components used in detergent compositions may be employed, such as soil-suspending agents, soil-release polymers, bactericides, coloring agents, foam control agents, corrosion inhibitors and perfumes.

Preferably, the liquid compositions according to the present invention are in "concentrated form"; in such case, the liquid detergent compositions according to the present invention will contain a lower amount of water, compared to conventional liquid detergents. The level of water is less than 50%, preferably less than 30% by weight of the detergent compositions.

Said concentrated products provide advantages to the consumer, who has a product which can be used in lower amounts and to the producer, who has lower shipping costs.

The liquid compositions are especially effective when applied directly to soils and stains in a pretreatment step before washing the fabrics.

The detergent compositions of the present invention can also be used as detergent additive products. Such additive products are intended to supplement or boost the performance of conventional detergent compositions.

The detergent compositions according to the present invention include compositions which are to be used for cleaning of substrates, such as fabrics, fibers, hard surfaces, skin etc., for example hard surface cleaning compositions (with or without abrasives), laundry detergent compositions, automatic and non-automatic dishwashing compositions.

Non-aqueous Heavy Duty Liquid Compositions

The manufacture of heavy duty liquid detergent compositions, especially those designed for fabric laundering, which comprise a non-aqueous carrier medium can be conducted in the manner disclosed in more detail hereinafter. In an alternate mode, such non-aqueous compositions can be prepared according to the disclosures of U.S. Pat. Nos. 4,753,570; 4,767,558; 4,772,413; 4,889,652; 4,892,673; GB-A-2,158,838; GB-A-2,195,125; GB-A-2,195,649; U.S. Pat. Nos. 4,988,462; 5,266,233; EP-A-225, 654 (Jun. 16, 1987); EP-A-510,762 (10/28/92); EP-A-540, 089 (5/5193); EP-A-540,090 (May 5, 1993); U.S. Pat. No. 4,615,820; EP-A-565,017 (Oct. 13, 1993); EP-A-030,096 (Jun. 10, 1981), incorporated herein by reference. Such compositions can contain various particulate detersive ingredients (including the bleaching agents, as disclosed hereinabove) stably suspended therein. Such non-aqueous compositions thus comprise a LIQUID PHASE and, optionally but preferably, a SOLID PHASE, all as described in more detail hereinafter and in the cited references. The mid-chain branched surfactant is incorporated in the compositions at the levels and in the manner described hereinabove for the manufacture of other laundry detergent compositions.

(1) Liquid Phase

The liquid phase will generally comprise from about 35% to 99% by weight of the detergent compositions herein. More preferably, the liquid phase will comprise from about 50% to 95% by weight of the compositions. Most preferably, the liquid phase will comprise from about 45% to 75% by weight of the compositions herein. The liquid phase of the detergent compositions herein essentially contains relatively high concentrations of a certain type anionic surfactant combined with a certain type of nonaqueous, liquid diluent.

(a) Essential Anionic Surfactant

The anionic surfactant essentially utilized as an essential component of the nonaqueous liquid phase is one selected from the alkali metal salts of alkylbenzene sulfonic acids in which the alkyl group contains from about 10 to 16 carbon atoms, in straight chain or branched chain configuration. (See U.S. Pat. Nos. 2,220,099 and 2,477,383, incorporated herein by reference.) Especially preferred are the sodium and potassium linear straight chain alkylbenzene sulfonates (LAS) in which the average number of carbon atoms in the alkyl group is from about 11 to 14. Sodium $C_{11}$–$C_{14}$ LAS is especially preferred.

The alkylbenzene sulfonate anionic surfactant will be dissolved in the nonaqueous liquid diluent which makes up the second essential component of the nonaqueous phase. To form the structured liquid phase required for suitable phase stability and acceptable rheology, the alkylbenzene sulfonate anionic surfactant is generally present to the extent of from about 30% to 65% by weight of the liquid phase. More preferably, the alkylbenzene sulfonate anionic surfactant will comprise from about 35% to 50% by weight of the nonaqueous liquid phase of the compositions herein. Utilization of this anionic surfactant in these concentrations corresponds to an anionic surfactant concentration in the total composition of from about 15% to 60% by weight, more preferably from about 20% to 40% by weight, of the composition.

(b) Nonaqueous Liquid Diluent

To form the liquid phase of the detergent compositions, the hereinbefore described alkylbenzene sulfonate anionic surfactant is combined with a nonaqueous liquid diluent which contains two essential components. These two components are a liquid alcohol alkoxylate material and a nonaqueous, low-polarity organic solvent.

i) Alcohol Alkoxylates

One essential component of the liquid diluent used to form the compositions herein comprises an alkoxylated fatty alcohol material. Such materials are themselves also nonionic surfactants. Such materials correspond to the general formula:

$$R^1(OC_mH_{2m})_nOH$$

wherein $R^1$ is a $C_8$–$C_{16}$ alkyl group, m is from 2 to 4, and n ranges from about 2 to 12. Preferably $R^1$ is an alkyl group, which may be primary or secondary, that contains from about 9 to 15 carbon atoms, more preferably from about 10 to 14 carbon atoms. Preferably also the alkoxylated fatty alcohols will be ethoxylated materials that contain from about 2 to 12 ethylene oxide moieties per molecule, more preferably from about 3 to 10 ethylene oxide moieties per molecule.

The alkoxylated fatty alcohol component of the liquid diluent will frequently have a hydrophilic-lipophilic balance (HLB) which ranges from about 3 to 17. More preferably, the HLB of this material will range from about 6 to 15, most preferably from about 8 to 15.

Examples of fatty alcohol alkoxylates useful as one of the essential components of the nonaqueous liquid diluent in the compositions herein will include those which are made from alcohols of 12 to 15 carbon atoms and which contain about 7 moles of ethylene oxide. Such materials have been commercially marketed under the trade names Neodol 25-7 and Neodol 23-6.5 by Shell Chemical Company. Other useful Neodols include Neodol 1-5, an ethoxylated fatty alcohol averaging 11 carbon atoms in its alkyl chain with about 5 moles of ethylene oxide; Neodol 23-9, an ethoxylated primary $C_{12}$–$C_{13}$ alcohol having about 9 moles of ethylene oxide and Neodol 91-10, an ethoxylated $C_9$–$C_{11}$ primary alcohol having about 10 moles of ethylene oxide. Alcohol ethoxylates of this type have also been marketed by Shell Chemical Company under the Dobanol tradename. Dobanol 91-5 is an ethoxylated $C_9$–$C_{11}$ fatty alcohol with an average of 5 moles ethylene oxide and Dobanol 25-7 is an ethoxylated $C_{12}$–$C_{15}$ fatty alcohol with an average of 7 moles of ethylene oxide per mole of fatty alcohol.

Other examples of suitable ethoxylated alcohols include Tergitol 15-S-7 and Tergitol 15-S-9 both of which are linear secondary alcohol ethoxylates that have been commercially marketed by Union Carbide Corporation. The former is a mixed ethoxylation product of $C_{11}$ to $C_{15}$ linear secondary alkanol with 7 moles of ethylene oxide and the latter is a similar product but with 9 moles of ethylene oxide being reacted.

Other types of alcohol ethoxylates useful in the present compositions are higher molecular weight nonionics, such as Neodol 45-11, which are similar ethylene oxide condensation products of higher fatty alcohols, with the higher fatty alcohol being of 14–15 carbon atoms and the number of ethylene oxide groups per mole being about 11. Such products have also been commercially marketed by Shell Chemical Company.

The alcohol alkoxylate component which is essentially utilized as part of the liquid diluent in the nonaqueous compositions herein will generally be present to the extent of from about 1% to 60% of the liquid phase composition. More preferably, the alcohol alkoxylate component will comprise about 5% to 40% of the liquid phase. Most preferably, the essentially utilized alcohol alkoxylate component will comprise from about 5% to 30% of the detergent composition liquid phase. Utilization of alcohol alkoxylate in these concentrations in the liquid phase corresponds to an alcohol alkoxylate concentration in the total composition of from about 1% to 60% by weight, more preferably from about 2% to 40% by weight, and most preferably from about 5% to 25% by weight, of the composition.

ii) Nonaqueous Low-Polarity Organic Solvent

A second essential component of the liquid diluent which forms part of the liquid phase of the detergent compositions herein comprises nonaqueous, low-polarity organic solvent (s). The term "solvent" is used herein to connote the non-surface active carrier or diluent portion of the liquid phase of the composition. While some of the essential and/or optional components of the compositions herein may actually dissolve in the "solvent"-containing liquid phase, other components will be present as particulate material dispersed within the "solvent"-containing liquid phase. Thus the term "solvent" is not meant to require that the solvent material be capable of actually dissolving all of the detergent composition components added thereto.

The nonaqueous organic materials which are employed as solvents herein are those which are liquids of low polarity. For purposes of this invention, "low-polarity" liquids are those which have little, if any, tendency to dissolve one of the preferred types of particulate material used in the compositions herein, i.e., the peroxygen bleaching agents, sodium perborate or sodium percarbonate. Thus relatively polar solvents such as ethanol should not be utilized. Suitable types of low-polarity solvents useful in the nonaqueous liquid detergent compositions herein do include non-vicinal $C_4$–$C_8$ alkylene glycols, alkylene glycol mono lower alkyl ethers, lower molecular weight polyethylene glycols, lower molecular weight methyl esters and amides, and the like.

A preferred type of nonaqueous, low-polarity solvent for use in the compositions herein comprises the non-vicinal $C_4$–$C_8$ branched or straight chain alkylene glycols. Materials of this type include hexylene glycol (4-methyl-2,4-pentanediol), 1,6-hexanediol, 1,3-butylene glycol and 1,4butylene glycol. Hexylene glycol is the most preferred.

Another preferred type of nonaqueous, low-polarity solvent for use herein comprises the mono-, di-, tri-, or tetra-$C_2$–$C_3$ alkylene glycol mono $C_2$–$C_6$ alkyl ethers. The specific examples of such compounds include diethylene glycol monobutyl ether, tetraethylene glycol monobutyl ether, dipropylene glycol monoethyl ether, and dipropylene glycol monobutyl ether. Diethylene glycol monobutyl ether and dipropylene glycol monobutyl ether are especially preferred.

Compounds of the type have been commercially marketed under the tradenames Dowanol, Carbitol, and Cellosolve.

Another preferred type of nonaqueous, low-polarity organic solvent useful herein comprises the lower molecular weight polyethylene glycols (PEGs). Such materials are those having molecular weights of at least about 150. PEGs of molecular weight ranging from about 200 to 600 are most preferred.

Yet another preferred type of non-polar, nonaqueous solvent comprises lower molecular weight methyl esters. Such materials are those of the general formula: $R^1$—C(O)—$OCH_3$ wherein $R^1$ ranges from 1 to about 18. Examples of suitable lower molecular weight methyl esters include methyl acetate, methyl propionate, methyl octanoate, and methyl dodecanoate.

The nonaqueous, low-polarity organic solvent(s) employed should, of course, be compatible and non-reactive with other composition components, e.g., bleach and/or activators, used in the liquid detergent compositions herein. Such a solvent component will generally be utilized in an amount of from about 1% to 70% by weight of the liquid phase. More preferably, the nonaqueous, low-polarity organic solvent will comprise from about 10% to 60% by weight of the liquid phase, most preferably from about 20% to 50% by weight, of the liquid phase of the composition. Utilization of this organic solvent in these concentrations in the liquid phase corresponds to a solvent concentration in the total composition of from about 1% to 50% by weight, more preferably from about 5% to 40% by weight, and most preferably from about 10% to 30% by weight, of the composition.

iii) Alcohol Alkoxylate To Solvent Ratio

The ratio of alcohol alkoxylate to organic solvent within the liquid diluent can be used to vary the rheological properties of the detergent compositions eventually formed. Generally, the weight ratio of alcohol alkoxylate to organic solvent will range from about 50:1 to 1:50. More preferably, this ratio will range from about 3:1 to 1:3.

iv) Liquid Diluent Concentration

As with the concentration of the alkylbenzene sulfonate anionic surfactant mixture, the amount of total liquid diluent in the nonaqueous liquid phase herein will be determined by the type and amounts of other composition components and by the desired composition properties. Generally, the liquid diluent will comprise from about 35% to 70% of the nonaqueous liquid phase of the compositions herein. More preferably, the liquid diluent will comprise from about 50% to 65% of the nonaqueous liquid phase. This corresponds to a nonaqueous liquid diluent concentration in the total composition of from about 15% to 70% by weight, more preferably from about 20% to 50% by weight, of the composition.

(2) Solid Phase

The nonaqueous detergent compositions herein also essentially comprise from about 1% to 65% by weight, more preferably from about 5% to 50% by weight, of a solid phase of particulate material which is dispersed and suspended within the liquid phase. Generally such particulate material will range in size from about 0.1 to 1500 microns. More preferably such material will range in size from about 5 to 200 microns.

The particulate material utilized herein can comprise one or more types of detergent composition components which in particulate form are substantially insoluble in the nonaqueous liquid phase of the composition. The types of particulate materials which can be utilized are described in detail as follows:

(3) Composition Preparation and Use

The nonaqueous liquid detergent compositions herein can be prepared by combining the essential and optional components thereof in any convenient order and by mixing, e.g., agitating, the resulting component combination to form the phase stable compositions herein. In a typical process for preparing such compositions, essential and certain preferred optional components will be combined in a particular order and under certain conditions.

In the first step of such a typical preparation process, an admixture of the alkylbenzene sulfonate anionic surfactant and the two essential components of the nonaqueous diluent is formed by heating a combination of these materials to a temperature from about 30° C. to 100° C.

In a second process step, the heated admixture formed as hereinbefore described is maintained under shear agitation at a temperature from about 40° C. to 100° C. for a period of from about 2 minutes to 20 hours. Optionally, a vacuum can be applied to the admixture at this point. This second process step serves to completely dissolve the anionic surfactant in the nonaqueous liquid phase.

In a third process step, this liquid phase combination of materials is cooled to a temperature of from about 0° C. to 35° C. This cooling step serves to form a structured, surfactant-containing liquid base into which the particulate material of the detergent compositions herein can be added and dispersed.

Particulate material is added in a fourth process step by combining the particulate material with the liquid base which is maintained under conditions of shear agitation. When more than one type of particulate material is to be added, it is preferred that a certain order of addition be observed. For example, while shear agitation is maintained, essentially all of any optional surfactants in solid particulate form can be added in the form of particles ranging in size from about 0.2 to 1,000 microns. After addition of any optional surfactant particles, particles of substantially all of an organic builder, e.g., citrate and/or fatty acid, and/or an alkalinity source, e.g., sodium carbonate, can be added while continuing to maintain this admixture of composition components under shear agitation. Other solid form optional ingredients can then be added to the composition at this point. Agitation of the mixture is continued, and if necessary, can be increased at this point to form a uniform dispersion of insoluble solid phase particulates within the liquid phase.

After some or all of the foregoing solid materials have been added to this agitated mixture, particles of bleaching agent can be added to the composition, again while the mixture is maintained under shear agitation. By adding the bleaching agent material last, or after all or most of the other components, and especially after alkalinity source particles, have been added, desirable stability benefits for the bleach can be realized.

The bleaching agents used herein can be any of the bleaching agents useful for detergent compositions in textile cleaning. These include oxygen bleaches as well as other bleaching agents such as percarboxylic acid bleaching agents and salts thereof. Suitable examples of this latter class of agents include magnesium monoperoxyphthalate hexahydrate, the magnesium salt of metachloro perbenzoic acid, 4-nonylamino-4-oxoperoxybutyric acid and diperoxydodecanedioic acid. Such bleaching agents are disclosed in U.S. Pat. No. 4,483,781, Hartman, issued Nov. 20, 1984, U.S. patent application Ser. No. 740,446, Burns et al, filed Jun. 3, 1985, European Patent Application 0,133,354, Banks et al, published Feb. 20, 1985, and U.S. Pat. No. 4,412,934, Chung et al, issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Preferred are peroxygen bleaching agents, which include sodium carbonate peroxyhydrate and equivalent "percarbonate" bleaches, perborate bleaches, sodium pyrophosphate peroxyhydrate, urea peroxyhydrate, sodium peroxide, and persulfate bleach (e.g., OXONE, manufactured commercially by DuPont).

If enzyme prills are incorporated, they are preferably added to the nonaqueous liquid matrix last.

As a final process step, after addition of all of the particulate material, agitation of the mixture is continued for a period of time sufficient to form compositions having the requisite viscosity and phase stability characteristics. Frequently this will involve agitation for a period of from about 1 to 30 minutes.

As a variation of the composition preparation procedure hereinbefore described, one or more of the solid components may be added to the agitated mixture as a slurry of particles premixed with a minor portion of one or more of the liquid components. Thus a premix of a small fraction of the alcohol alkoxylate and/or nonaqueous, low-polarity solvent with particles of the organic builder material and/or the particles of the inorganic alkalinity source and/or particles of a bleach activator may be separately formed and added as a slurry to the agitated mixture of composition components. Addition of such slurry premixes should precede addition of bleaching agent and/or enzyme particles which may themselves be part of a premix slurry formed in analogous fashion.

The compositions of this invention, prepared as hereinbefore described, can be used to form aqueous washing solutions for use in the laundering and bleaching of fabrics. Generally, an effective amount of such compositions is added to water, preferably in a conventional fabric laundering automatic washing machine, to form such aqueous laundering solutions. The aqueous washing solution so formed is then contacted, preferably under agitation, with the fabrics to be laundered therewith.

An effective amount of the liquid detergent compositions herein added to water to form aqueous laundering solutions can comprise amounts sufficient to form from about 500 to 7,000 ppm of composition in aqueous solution. More preferably, from about 800 to 3,000 ppm of the detergent compositions herein will be provided in aqueous washing solution.

In the following Examples, the abbreviations for the various ingredients used for the compositions have the following meanings.

| | |
|---|---|
| LAS | Sodium linear $C_{12}$ alkyl benzene sulfonate |
| $MBAS_x$ | Mid-chain branched primary alkyl (average total carbons = x) sulfate |
| $MBAE_xS_z$ | Mid-chain branched primary alkyl (average total carbons = z) ethoxylate (average EO = x) sulfate, sodium salt |
| $MBAE_x$ | Mid-chain branched primary alkyl (average total carbons = x) ethoxylate (average EO = 8) |
| $CxyE_zS$ | Sodium $C_{1x}$–$C_{1y}$ branched alkyl sulfate condensed with z moles of ethylene oxide |
| CxyFA | $C_{1x}$–$C_{1y}$ fatty acid |
| CxyEz | A $C_{1x}$–$C_{1y}$ branched primary alcohol condensed with an average of z moles of ethylene oxide |
| C24 N-Me Glucamide | $C_{12}$–$C_{14}$ N-methyl glucamide |
| CxAPA | Alkyl amido propyl amine |
| Citric acid | Anhydrous citric acid |

| | |
|---|---|
| Carbonate | Anhydrous sodium carbonate with a particle size between 200 μm and 900 μm |
| Citrate | Tri-sodium citrate dihydrate of activity 86.4% with a particle size distribution between 425 μm and 850 μm |
| Protease | Proteolytic enzyme of activity 4KNPU/g sold by NOVO Industries A/S under the tradename Savinase |
| Cellulase | Cellulytic enzyme of activity 1000 CEVU/g sold by NOVO Industries A/S under the tradename Carezyme |
| Amylase | Amylolytic enzyme of activity 60 KNU/g sold by NOVO Industries A/S under the tradename Termamyl 60T |
| Lipase | Lipolytic enzyme of activity 100 kLU/g sold by NOVO Industries A/S under the tradename Lipolase |
| Endolase | Endoglunase enzyme of activity 3000 CEVU/g sold by NOVO Industries A/S |
| PB1 | Anhydrous sodium perborate bleach of nominal formula $NaBO_2.H_2O_2$ |
| NOBS | Nonanoyloxybenzene sulfonate in the form of the sodium salt. |
| DTPMP: phosphonate), | Diethylene triamine penta (methylene marketed by Monsanto under the Trade name Dequest 2060 |
| MEA | Monoethanolamine |
| PG | Propanediol |
| EtOH | Ethanol |
| Brightener 1 | Disodium 4,4'-bis(2-sulphostyryl)biphenyl |
| Brightener 2 triazin- | Disodium 4,4'-bis(4-anilino-6-morpholino-1.3.5-2-yl)amino) stilbene-2:2'-disulfonate. |
| Silicone antifoam: | Polydimethylsiloxane foam controller with siloxane-oxyalkylene copolymer as dispersing agent with a ratio of said foam controller to said dispersing agent of 10:1 to 100:1. |
| NaOH | Solution of sodium hydroxide |
| DTPA | Diethylene triamine pentaacetic acid |
| NaTS | Sodium toluene sulfonic acid |

EXAMPLE 1

A non-limiting example of bleach-containing nonaqueous liquid laundry detergent is prepared having the composition as set forth in Table I.

TABLE I

| Component | Wt. % | Range (% wt.) |
|---|---|---|
| Liquid Phase | | |
| LAS | 25.0 | 18–35 |
| $C_{24}$ E5 or $MBAE_{15}$ | 13.6 | 10–20 |
| Hexylene glycol | 27.3 | 20–30 |
| Perfume | 0.4 | 0–1.0 |
| $MBAB_2S_{15.5}$ | 2.3 | 1–3.0 |
| Solids | | |
| Protease | 0.4 | 0–1.0 |
| Citrate | 4.3 | 3–6 |
| PB1 | 3.4 | 2–7 |
| NOBS | 8.0 | 2–12 |
| Carbonate | 13.9 | 5–20 |
| DTPA | 0.9 | 0–1.5 |
| Brightener 1 | 0.4 | 0–0.6 |
| Silicone antifoam | 0.1 | 0–0.3 |
| Minors | Balance | — |

The resulting composition is an anhydrous heavy duty liquid laundry detergent which provides excellent stain and soil removal performance when used in normal fabric laundering operations.

EXAMPLE 2

The following Example further illustrates the invention herein with respect to a hand dishwashing liquid.

| Ingredient | % (wt.) | Range (% wt.) |
|---|---|---|
| $MBAE1_5$ | 2.0 | 0.15–3 |
| $MBAE_2S_{15}$ | 2.0 | 0.5–10 |
| C24 N-methyl glucamide | 3.0 | 1.0–10 |
| Ammonium $C_{12-13}$ alkyl sulfate | 7.0 | 2–35 |
| $C_{12-C14}$ ethoxy (1) sulfate | 20.5 | 5–35 |
| Coconut amine oxide | 2.6 | 2–5 |
| Betaine/Tetronic 704 ®** | 0.87–0.10 | 0–2 (mix) |
| Alcohol Ethoxylate $C_{9-11}E_9$ | 5.0 | 0.5–10 |
| Ammonium xylene sulfonate | 4.0 | 1–6 |
| Ethanol | 4.0 | 0–7 |
| Ammonium citrate | 0.06 | 0–1.0 |
| Magnesium chloride | 3.3 | 0–4.0 |
| Calcium chloride | 2.5 | 0–4.0 |
| Ammonium sulfate | 0.08 | 0–4.0 |
| Hydrogen peroxide | 200 ppm | 0–300 ppm |
| Perfume | 0.18 | 0–0.5 |
| Maxatase ® protease | 0.50 | 0–1.0 |
| Water and minors | - - - Balance - - - | |

** Cocoalkyl betaine.

EXAMPLE 3

Liquid detergent compositions are made according to the following.

| | % by weight of the detergent compositions | | | |
|---|---|---|---|---|
| | A | B | C | D |
| $C_{25}$ AE3S | 2 | 8 | 7 | 5 |
| $MBAS_{15}$ | 6 | 4 | 8 | 1 |
| $C_{12}-C_{14}$ alkyldimethyl amine oxide | — | — | — | 2 |
| $C_{25}$ AS | 15 | 12 | 8 | 8 |
| $C_{24}$ N-methyl glucamide | 5 | 4 | 3 | 3 |
| $C_{24}$ AE5 | 6 | 1 | 1 | 1 |
| $C_{12-C18}$ fatty acid | 11 | 4 | 4 | 3 |
| Citric acid | 1 | 3 | 3 | 2 |
| DTPMP | 1 | 1 | 1 | 0.5 |
| MEA | 8 | 5 | 5 | 2 |
| NaOH | 1 | 2.5 | 1 | 1.5 |
| PG | 14.5 | 13.1 | 10.0 | 8 |
| EtOH | 1.8 | 4.7 | 5.4 | 1 |
| Amylase (300 KNU/g) | 0.1 | 0.1 | 0.1 | 0.1 |
| Lipase D96/L (100 KNU/g) | 0.15 | 0.15 | 0.15 | 0.15 |
| Protease (35 g/l) | 0.5 | 0.5 | 0.5 | 0.5) |
| Endolase | 0.05 | 0.05 | 0.05 | 0.05 |
| Cellulase | 0.09 | 0.09 | 0.09 | 0.09 |
| Terephthalate-based polymer | 0.5 | — | 0.3 | 0.3 |
| Boric acid | 2.4 | 2.8 | 2.8 | 2.4 |
| Sodium xylene sulfonate | — | 3 | — | — |
| 2-butyl-octanol | 1 | 1 | 1 | 1 |
| Branched silicone | 0.3 | 0.3 | 0.3 | 0.3 |
| Water & minors | Up to 100% | | | |

The above liquid detergent compositions (A–D) are found to be very efficient in the removal of a wide range of stains and soils from fabrics under various usage conditions.

EXAMPLES 4–9

The following are heavy duty liquid laundry detergent compositions according to the present invention.

| Example#: | 4 | 5 | 6 | 7 | 8 | 9 |
|---|---|---|---|---|---|---|
| $MBAS_{15.5}$ or $MBAE_2S_{15}$ | 7.0 | 7.0 | 7.0 | 7.0 | 7.0 | 7.0 |
| C25 AS | 10 | 8.0 | — | — | 5.0 | 5.0 |

-continued

| Example#: | 4 | 5 | 6 | 7 | 8 | 9 |
|---|---|---|---|---|---|---|
| C35AE3S/C25AE3S | 2.0 | 9.0 | — | — | 7.0 | 7.0 |
| C24 N-Me Glucamide | 6.0 | 5.0 | 4.5 | 3.7 | 4.0 | 4.0 |
| C35 E7 | 6.0 | 1.0 | — | — | — | — |
| C25 AE2.5S | — | — | 12.0 | 12.0 | — | — |
| C23 E9 | — | — | 2.0 | 1.0 | 5.0 | 5.0 |
| C10 APA | — | 1.5 | — | 2.0 | — | 2.5 |
| C24 Fatty Acid | 7.5 | 1.1 | 2.0 | 4.0 | 5.0 | 5.0 |
| C48 Fatty Acid | 3.0 | 3.5 | — | — | — | — |
| Citric Acid | 1.0 | 3.5 | 3.0 | 3.0 | 3.0 | 3.0 |
| Protease (34 g/#) | 0.6 | 0.6 | 0.9 | 0.9 | 1.2 | 1.2 |
| Lipase | 0.1 | 0.1 | 0.1 | 0.1 | 0.2 | 0.2 |
| Amylase (300 KMU/g) | 0.1 | 0.1 | 0.1 | 0.1 | — | 0.1 |
| Cellulase | 0.03 | 0.03 | 0.05 | 0.05 | 0.2 | 0.2 |
| Endolase | 0.1 | 0.1 | — | — | — | — |
| Brightener 2 | 0.1 | 0.1 | — | — | — | — |
| Boric Acid | 3.0 | 3.0 | 3.5 | 3.5 | 4.0 | 4.0 |
| MEA | 8.0 | 4.0 | 1.0 | 1.5 | 7.0 | 7.0 |
| NaOH | 1.0 | 4.0 | 3.0 | 2.5 | 1.0 | 1.0 |
| PG | 12.0 | 12.0 | 7.5 | 7.5 | 7.0 | 7.0 |
| EtOH | 1.0 | 1.0 | 3.5 | 3.5 | 6.0 | 6.0 |
| NaTS | — | — | 2.5 | 2.5 | — | — |
| Minors | - - - Balance - - - | | | | | |

Shampoo Compositions

The shampoo compositions of the present invention typically can comprise the following ingredients, components, or limitations described herein. As used herein, "water soluble" refers to any material that is sufficiently soluble in water to form a substantially clear solution to the naked eye at a concentration of 0.1% in water, i.e. distilled or equivalent, at 25° C.

Detersive Co-Surfactant

The shampoo compositions of the present invention will comprise, in addition to the mid-chain branched surfactant, one or more detersive co-surfactants selected from the group consisting of anionic surfactant, nonionic surfactant, cationic surfactant, amphoteric surfactant, zwitterionic surfactants, and mixtures thereof. The shampoo compositions preferably comprise an anionic co-surfactant. Surfactant mixture (i.e., the mid-chain branched surfactant plus the co-surfactant) concentrations range from about 5% to about 50%, preferably from about 8% to about 30%, more preferably from about 10% to about 25%, by weight of the compositions.

Anionic Surfactant

The shampoo compositions preferably comprise an anionic co-surfactant, and preferably at concentrations of from about 5% to about 30%, more preferably from about 7% to about 25%, even more preferably from about 7% to about 20%, and most preferably from about 9% to about 18%, by weight of the composition.

Anionic surfactants for use in the shampoo compositions include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to 10, and M is a cation such as ammonium, alkanolamines, such as triethanolamine, monovalent metals, such as sodium and potassium, and polyvalent metal cations, such as magnesium, and calcium. The cation M, of the anionic surfactant should be chosen such that the anionic surfactant component is water soluble. Solubility will depend upon the particular anionic surfactants and cations chosen.

Preferably, R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil or tallow, or can be synthetic. Lauryl alcohol and straight chain alcohols derived from coconut oil are preferred herein. Such alcohols are reacted with between about 0 and about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the shampoo compositions of the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants are the water-soluble salts of organic, sulfuric acid reaction products of the general formula [$R_1$—$SO_3$—M] where $R_1$ is selected from the group consisting of a straight or branched chain, saturated aliphatic hydrocarbon radical having from about 8 to about 24, preferably about 10 to about 18, carbon atoms; and M is a cation, as previously described, subject to the same limitations regarding polyvalent metal cations as previously discussed. Examples of such surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $S_3$, $H_2SO_4$, obtained according to known sulfonation methods, including bleaching and hydrolysis. Preferred are alkali metal and ammonium sulfonated $C_{10-18}$ n-paraffins.

Still other suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other similar anionic surfactants are described in U.S. Pat. Nos. 2,486,921; 2,486,922; and 2,396,278.

Other anionic surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid.

Other suitable anionic surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, which description is incorporated herein by reference.

Another class of anionic surfactants suitable for use in the shampoo compositions are the beta-alkyloxy alkane sulfonates. These compounds have the following formula:

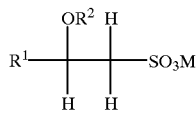

where $R^1$ is a straight chain alkyl group having from about 6 to about 20 carbon atoms, $R^2$ is a lower alkyl group having from about 1 (preferred) to about 3 carbon atoms, and M is a water-soluble cation as hereinbefore described.

Many other anionic surfactants suitable for use in the shampoo compositions are described in *McCutcheon's, Emulsifiers and Detergents*, 1989 Annual, published by M. C. Publishing Co., and in U.S. Pat. No. 3,929,678, which descriptions are incorporated herein by reference.

Preferred anionic surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric and zwitterionic surfactants

The detersive surfactant of the shampoo compositions may comprise an amphoteric and/or zwitterionic surfactant. Concentrations of such surfactants will generally range from about 0.5% to about 20%, preferably from about 1% to about 10%, by weight of the shampoo compositions.

Amphoteric surfactants for use in the shampoo compositions include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic surfactants for use in the shampoo compositions include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

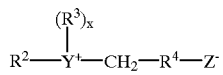

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines and amidosultaines can be used as foam enhancing surfactants that are mild to the eye in partial replacement of anionic surfactants. Sultaines, including amidosultaines, include for example, cocodimethylpropylsultaine, stearyldimethylpropylsultaine, lauryl-bis-(2-hydroxyethyl) propylsultaine and the like; and the amidosultaines such as cocoamidodimethylpropylsultaine, stearylamidododimethylpropylsultaine, lauryl-amidobis-(2-hydroxyethyl) propylsultaine, and the like. Preferred are amidohydroxysultaines such as the $C_{12}-C_{18}$ hydrocarbyl amidopropyl hydroxy-sultaines, especially $C_{12}-C_{14}$ hydrocarbyl amido propyl hydroxysultaines, e.g., laurylamidopropyl hydroxysultaine and cocamidopropyl hydroxysultaine. Other sultaines are described in U.S. Pat. No. 3,950,417, which descriptions are incorporated herein by reference.

Other suitable amphoteric surfactants are the aminoalkanoates of the formula $R-NH(CH_2)_nCOOM$, the iminodialkanoates of the formula

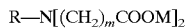

and mixtures thereof; wherein n and m are numbers from 1 to 4, R is $C_8-C_{22}$ alkyl or alkenyl, and M is hydrogen, alkali metal, alkaline earth metal, ammonium or alkanolammonium.

Examples of suitable aminoalkanoates include n-alkylamino-propionates and n-alkyliminodipropionates, specific examples of which include N-lauryl-beta-amino propionic acid or salts thereof, and N-lauryl-beta-imino-dipropionic acid or salts thereof, and mixtures thereof.

Other suitable amphoteric surfactants include those represented by the formula:

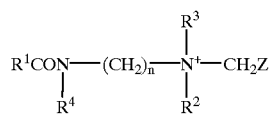

wherein $R^1$ is $C_8-C_{22}$ alkyl or alkenyl, preferably $C_{12}-C_{16}$, $R^2$ is hydrogen or $CH_2CO_2M$, $R^3$ is $CH_2CH_2OH$ or $CH_2CH_2OCH_2CH_2COOM$, $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal (e.g., lithium, sodium, potassium), alkaline earth metal (beryllium, magnesium, calcium, strontium, barium), or ammonium. This type of surfactant is sometimes classified as an imidazoline-type amphoteric surfactant, although it should be recognized that it does not necessarily have to be derived, directly or indirectly, through an imidazoline intermediate.

Suitable materials of this type are marketed under the trade name MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine surfactants (zwitterionic) suitable for use in the shampoo compositions are those represented by the formula:

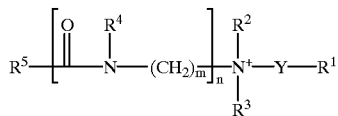

wherein:

$R^1$ is a member selected from the group consisting of

$R_2$ is lower alkyl or hydroxyalkyl;
$R_3$ is lower alkyl or hydroxyalkyl;
$R_4$ is a member selected from the group consisting of hydrogen and lower alkyl;
$R_5$ is higher alkyl or alkenyl;
Y is lower alkyl, preferably methyl;
m is an integer from 2 to 7, preferably from 2 to 3;
n is the integer 1 or 0;
M is hydrogen or a cation, as previously described, such as an alkali metal, alkaline earth metal, or ammonium.

The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substitutents such as hydroxyl or halogen radicals wherein the radical remains of hydrophobic character.

Examples of surfactant betaines of the above formula wherein n is zero which are useful herein include the alkylbetaines such as cocodimethylcarboxymethylbetaine, lauryldimethylcarboxymethylbetaine, lauryl dimethyl-alpha-carboxyethylbetaine, cetyldimethylcarboxymethylbetaine, lauryl-bis-(2-hydroxyethyl)carboxymethylbetaine, stearyl-bis-(2-hydroxy-propyl)carboxymethylbetaine, oleyldimethyl-gammacarboxypropylbetaine, lauryl-bix-(2-hydroxypropyl) alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Specific examples of amido betaines and amidosulfo betaines useful in the shampoo compositions include the amidocarboxybetaines, such as cocoamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocoamido-bis-(2-hydroxyethyl)-carboxymethylbetaine, etc. The amido sulfobetaines may be represented by cocoamidodimethylsulfopropylbetaine, stearylamidodimethylsulfopropylbetaine, laurylamido-bis-(2-hydroxyethyl)-sulfopropylbetaine, and the like.

Nonionic surfactant

The shampoo compositions of the present invention may comprise a nonionic surfactant as the detersive surfactant component therein. Nonionic surfactants include those compounds produced by condensation of alkylene oxide groups (hydrophilic in nature) with an organic hydrophobic compound, which may be aliphatic or alkyl aromatic in nature.

Preferred nonionic surfactants for use in the shampoo compositions include the following:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) long chain tertiary amine oxides of the formula $[R^1R^2R^3N\rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula $[RR'R''P\rightarrow O]$ where R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms;

(6) long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety;

(7) alkyl polysaccharide (APS) surfactants (e.g. alkyl polyglycosides), examples of which are described in U.S. Pat. No. 4,565,647, which description is incorporated herein by reference, and which discloses APS surfactants having a hydrophobic group with about 6 to about 30 carbon atoms and polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); and (8) polyethylene glycol (PEG) glyceryl fatty esters, such as those of the formula $R(O)OCH^2CH(OH)CH^2(OCH^2CH^2)_n H$ wherein n is from about 5 to about 200, preferably from about 20 to about 100, and R is an aliphatic hydrocarbyl having from about 8 to about 20 carbon atoms.

Cationic Surfactants

Optional cationic surfactants for use as hair conditioning agents in the shampoo compositions will typically contain quaternary nitrogen moieties. Examples of suitable cationic surfactants are described in following documents, all of which are incorporated by reference herein in their entirety: M.C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591; U.S. Pat. No. 3,929,678; U.S. Pat. No. 3,959,461 and U.S. Pat. No. 4,387,090.

Examples of suitable cationic surfactants are those corresponding to the general formula:

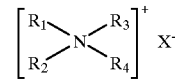

wherein $R_1$, $R_2$, $R_3$, and $R_4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R_1$, $R_2$, $R_3$, and $R_4$ are independently selected from C1 to about C22 alkyl. Especially preferred are cationic materials containing two long alkyl chains and two short alkyl chains or those containing one long alkyl chain and three short alkyl chains. The long alkyl chains in the compounds described in the previous sentence have from about 12 to about 22 carbon atoms, preferably from about 16 to about 22 carbon atoms, and the short alkyl chains in the compounds described in the previous sentence have from 1 to about 3 carbon atoms, preferably from 1 to about 2 carbon atoms.

Silicone Hair Conditioning Agent

The shampoo compositions of the present invention preferably also comprise a silicone hair conditioning agent at concentrations effective to provide hair conditioning benefits. Such concentrations range from about 0.05% to about 10%, preferably from about 0.1% to about 8%, more preferably from about 0.1% to about 5%, most preferably from about 0.2% to about 3%, by weight of the shampoo compositions.

The silicone hair conditioning agents for use in the shampoo compositions are insoluble in the shampoo compositions, and are preferably nonvolatile. Typically it will be intermixed in the shampoo composition so as to be in the form of a separate, discontinuous phase of dispersed, insoluble particles, also referred to as droplets. These droplets are suspended with a suspending agent described hereinafter. The silicone hair conditioning agent phase will comprise a silicone fluid hair conditioning agent such as a silicone fluid and can also comprise other ingredients, such as a silicone resin to enhance silicone fluid deposition efficiency or enhance glossiness of the hair (especially when high refractive index (e.g. above about 1.46) silicone conditioning agents are used (e.g. highly phenylated silicones).

As used herein, "nonvolatile" refers to silicone material with little or no significant vapor pressure under ambient conditions, as is understood by those in the art. Boiling point under one atmosphere (atm) will preferably be at least about 250° C., more preferably at least about 275° C., most preferably at least about 300° C. Vapor pressure is preferably about 0.2 mm HG at 25° C. or less, preferably about 0.1 mm HG at 25° C. or less.

The silicone hair conditioning agent phase may comprise volatile silicone, nonvolatile silicone, or mixtures thereof. Typically, if volatile silicones are present, it will be incidental to their use as a solvent or carrier for commercially available forms of nonvolatile silicone materials ingredients, such as silicone gums and resins.

The silicone hair conditioning agents for use in the shampoo compositions preferably have a viscosity of from about 20 to about 2,000,000 centistokes, more preferably from about 1,000 to about 1,800,000 centistokes, even more preferably from about 50,000 to about 1,500,000 centistokes, most preferably from about 100,000 to about 1,500,000 centistokes, at 25° C. The viscosity can be measured by means of a glass capillary viscometer as set forth in Dow Corning Corporate Test Method CTM0004, Jul. 20, 1970.

Silicone fluid for use in the shampoo compositions includes silicone oil which are flowable silicone materials with a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used.

Silicone oils for use in the composition include polyalkyl or polyaryl siloxanes of the following structure (I)

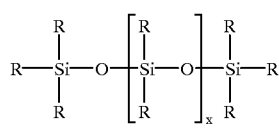

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions, and are capable of being deposited on and, of conditioning, the hair.

The two R groups on the silicon atom of each monomeric silicone unit may represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl -3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Suitable alkylamino substituted silicones include those represented by the following structure (II)

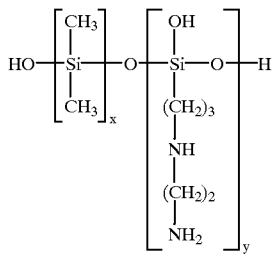

wherein x and y are integers which depend on the molecular weight, the average molecular weight being approximately between 5,000 and 10,000. This polymer is also known as "amodimethicone".

Suitable cationic silicone fluids include those represented by the formula (III):

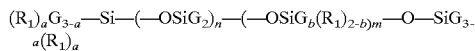

in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical of formula $CqH_{2q}$ L in which q is an integer from 2 to 8 and L is chosen from the groups

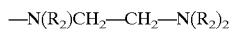

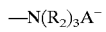

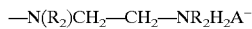

in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred cationic silicone corresponding to formula (III) is the polymer known as "trimethylsilylamodimethicone", of formula (IV):

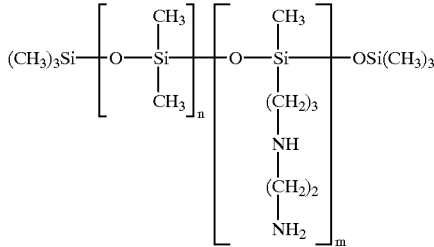

Other silicone cationic polymers which can be used in the shampoo compositions are represented by the formula (V):

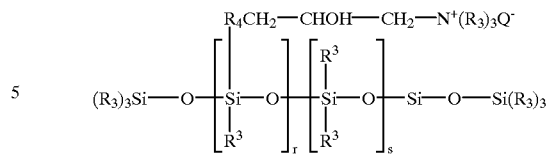

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56"

Other suitable silicone fluids for use in the silicone conditioning agents are insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones*, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

The silicone hair conditioning agent preferably comprises a mixture of polydimethylsiloxane gum (viscosity greater than about 1,000,000 centistokes) and polydimethylsiloxane oil (viscosity from about 10 to about 100,000 centistokes), wherein the ratio of gum to fluid is from about 30:70 to about 70:30, preferably from about 40:60 to about 60:40.

Another category of nonvolatile, insoluble silicone fluid conditioning agents are high refractive index silicones, having a refractive index of at least about 1.46, preferably at least about 1.48, more preferably at least about 1.52, most preferably at least about 1.55. Although not intended to necessarily be limiting, the refractive index of the polysiloxane fluid will generally be less than about 1.70, typically less than about 1.60. Polysiloxane "fluid" includes oils as well as gums.

The high refractive index polysiloxane fluid suitable for purposes hereof includes those represented by general Formula (I) above, as well as cyclic polysiloxanes such as those represented by Formula (VI) below:

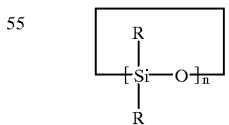

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/$cm^2$, typically at least about 27 dynes/$cm^2$. Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2NH2$ where each $R^1$ and $R^2$ independently is a $C_1$–$C_3$ alkyl, alkenyl, and/or alkoxy. High refractive index polysiloxanes are available from Dow Corning Corporation (Midland, Mich., U.S.A.) Huls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

Also, the spreading agent will preferably reduce the surface tension by at least about 2 dynes/$cm^2$, preferably at least about 3 dynes/$cm^2$, even more preferably at least about 4 dynes/$cm^2$, most preferably at least about 5 dynes/$cm^2$.

The surface tension of the mixture of the polysiloxane fluid and the spreading agent, at the proportions present in the final product, is preferably 30 dynes/$cm_2$ or less, more preferably about 28 dynes/$cm^2$ or less most preferably about 25 dynes/$cm^2$ or less. Typically the surface tension will be in the range of from about 15 to about 30, more typically from about 18 to about 28, and most generally from about 20 to about 25 dynes/$cm^2$.

The weight ratio of the highly arylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios may be effective due to the efficiency of these surfactants. Thus is contemplated that ratios significantly above 1000:1 may be used.

References disclosing examples of some suitable silicone fluids for use in the shampoo compositions include U.S. Pat. No. 2,826,551, U.S. Pat. No. 3,964,500, U.S. Pat. No. 4,364,837, British Patent 849,433, and *Silicon Compounds*, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetrafunctional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

Polyalkylene Glycol

The shampoo compositions of the present invention may further comprise selected polyalkylene glycols in amounts effective to enhance lather performance and enhance spreadability of the shampoo compositions on hair. Effective concentrations of the selected polyethylene glycols range from about 0.025% to about 1.5%, preferably from about 0.05% to about 1%, more preferably from about 0.1% to about 0.5%, by weight of the shampoo compositions.

For example, polyalkylene glycols suitable for use in the shampoo compositions are characterized by the general formula:

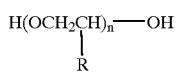

wherein R is hydrogen, methyl or mixtures thereof, preferably hydrogen, and n is an integer having an average value of from about 1,500 to about 25,000, preferably from about 2,500 to about 20,000, and more preferably from about 3,500 to about 15,000. When R is hydrogen, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist.

Specific examples of suitable polyethylene glycol polymers include PEG-2M wherein R equals hydrogen and n has an average value of about 2,000 (PEG 2-M is also known as Polyox WSR® N-10, which is available from Union Carbide and as PEG-2,000); PEG-5M wherein R is hydrogen and n has an average value of about 5,000 (PEG 5-M is also known as Polyox WSR® N-35 and Polyox WSR® N-80, both available from Union Carbide and as PEG-5,000 and Polyethylene Glycol 300,000); PEG-7M wherein R is hydrogen and n has an average value of about 7,000 (PEG 7-M is also known as Polyox WSR® N-750 available from Union Carbide); PEG-9M wherein R is hydrogen and n has an average value of about 9,000 (PEG 9-M is also known as Polyox WSR® N-3333 available from Union Carbide); and PEG-14 M wherein R is hydrogen and n has an average value of about 14,000 (PEG 14-M is also known as Polyox WSR® N-3000 available from Union Carbide).

Suitable polyalkylene polymers include polypropylene glycols and mixed polyethylene/polypropylene glycols.

Suspending Agent

The shampoo compositions of the present invention may further comprise a suspending agent at concentrations effective for suspending the silicone hair conditioning agent in dispersed form in the shampoo compositions. Such concentrations range from about 0.1% to about 10%, preferably from about 0.3% to about 5.0%, by weight of the shampoo compositions.

Suitable suspending agents include acyl derivatives, long chain amine oxides, and mixtures thereof, concentrations of which range from about 0.1% to about 5.0%, preferably from about 0.5% to about 3.0%, by weight of the shampoo compositions. When used in the shampoo compositions, these suspending agents are present in crystalline form. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide amide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na and K salts), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$–$C_{22}$) dimethyl amine oxides, e.g., stearyl dimethyl amine oxide Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940,941, and 956, available from B. F. Goodrich Company.

A carboxyvinyl polymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to produce carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids of the structure

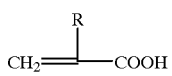

where R is a substituent selected from the group consisting of hydrogen and lower alkyl groups; most preferred is acrylic acid.

Preferred carboxyvinyl polymers have a molecular weight of at least about 750,000; more preferred are carboxyvinyl polymers having a molecular weight of at least about 1,250,000; most preferred are carboxyvinyl polymers having a molecular weight of at least about 3,000,000.

Other suitable suspending agents include nonionic suspending agents.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydorxethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Water

The shampoo compositions of the present invention comprise from about 20% to about 94.8%, preferably from about 50% to about 94.8%, more preferably from about 60% to about 85%, by weight of water.

Additional Hair Conditioning Agents

The shampoo compositions of the present invention may further comprise water soluble cationic polymeric conditioning agents, hydrocarbon conditioning agents, and mixtures thereof.

Cationic polymer

Optional cationic polymers for use as hair conditioning agents are those having a weight average molecular weight of from about 5,000 to about 10 million, and will generally have cationic nitrogen-containing moieties such as quaternary ammonium or cationic amino moieties, and mixtures thereof. Cationic charge density should be at least about 0.1 meq/gram, preferably less than about 3.0 meq/gram, which can be determined according to the well known Kjeldahl Method. Those skilled in the art will recognize that the charge density of amino-containing polymers can vary depending upon pH and the isoelectric point of the amino groups. The charge density should be within the above limits at the pH of intended use. Any anionic counterions can be utilized for the cationic polymers so long as the water solubility criteria is met.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in *International Cosmetic Ingredient Dicitonary*, Fifth Edition, 1993, which is incorporated by reference herein in its entirety.

Suitable optional cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic armines can be primary, secondary, or tertiary amines, depending upon the particular species and the pH of the composition. In general, secondary and tertiary amines, especially tertiary amines, are preferred. The cationic polymers can comprise mixtures of monomer units derived from amine- and/or quaternary ammonium-substituted monomer and/or compatible spacer monomers.

Other cationic polymers that can be used include polysaccharide polymers, such as cationic cellulose derivatives, cationic starch derivative, and cationic guar gum derivatives. Other materials include quaternary nitrogen-containing cellulose ethers as described in U.S. Pat. No. 3,962,418, and copolymers of etherified cellulose and starch as described in U.S. Pat. No. 3,958,581, which descriptions are incorporated herein by reference.

The shampoo compositions of the present invention may comprise one or more optional ingredients to improve or otherwise modify a variety of product characteristics, including aesthetics, stability and use benefits. Many such optional ingredients are known in the art and may be used in the shampoo compositions herein, provided that such ingredients are compatible with the essential ingredients described herein, or do not otherwise unduly impair cleansing or conditioning performance of the shampoo compositions.

The shampoo compositions of the present invention are intended for application to the hair and scalp, and will typically be applied using the hands and fingers. The shampoo compositions must therefore be safe and suitable for frequent (e.g. daily) use. Ingredients unsuitable for such frequent application should not be used at levels which would be unacceptable for frequent use, or which could cause undue irritation or damage to the hair or skin. The shampoo compositions of the present invention are therefore essentially free of such materials.

Optional materials include foam boosters, preservatives, thickeners, cosurfactants, dyes, perfumes, solvents, styling polymers, anti-static agents, anti-dandruff aids, and pediculocides.

Preferred optional materials include foam boosters, especially fatty ester (e.g. C8–C22) mono- and di (C1–C5, especially C1–C3) alkanol amides, specific examples of which include coconut monoethanolamide and coconut diethanolamide.

Examples of other suitable optional materials include preservatives such as benzyl alcohol, methyl paraben, propyl paraben and imidazolidinyl urea; fatty alcohols; block polymers of ethylene oxide and propylene oxide such as Pluronic F88 offered by BASF Wyandotte; sodium chloride, sodium sulfate; ammonium xylene sulfonate; propylene glycol; polyvinyl alcohol; ethyl alcohol; pH adjusting agents such as citric acid, succinic acid, phosphoric acid, sodium hydroxide, sodium carbonate, etc.; perfumes; and dyes.

Optional anti-static agents such as water-insoluble cationic surfactants may also be used, but should not unduly interfere with the in-use performance and end-benefits of the shampoo composition; particularly, the anti-static agent should not interfere with the anionic detersive surfactant. Suitable anti-static agents include tricetyl methyl ammonium chloride. Concentrations of such agents can range from about 0.1% to about 5% by weight of the shampoo compositions.

Optional antidandruff agents include particulate antidandruff agents such as pyridinethione salts, selenium compounds such as selenium disulfide, and soluble antidandruff agents. Concentrations of optional antidandruff agents range from about 0.1% to about 4%, preferably about 0.2% to about 2%, by weight of the shampoo compositions.

EXAMPLES 10–14

The compositions illustrated in Examples 10–14 illustrate specific embodiments of the shampoo compositions of the present invention, but are not intended to be limiting thereof Other modifications can be undertaken by the skilled artisan without departing from the spirit and scope of this invention. The compositions illustrated in Examples 10–14 may be prepared in the following manner (all percentages are based on weight unless otherwise specified).

First, a silicone premix is prepared by adding 70% dimethicone, 29% ammonium laureth-2 sulfate (solution basis, 26% active) and 1% sodium chloride, all by weight of the silicone premix, to a high shear mixing vessel and mixing for about 30 minutes or until the desired silicone particle size is achieved (typically a number average particle size of from about 5 microns to about 25 microns). A conventional silicon emulsion may also be used.

For each of the compositions illustrated in Examples 10–14, about one-third to all of the total mid-chain branched surfactant surfactant is added to a jacketed mix tank and heated to about 74° C. with slow agitation to form a surfactant solution. Cocamide monoethanolamide and fatty alcohol, as applicable, are added to the tank and allowed to disperse. Ethylene glycol distearate (EGDS) is then added to the mixing vessel, and melted. After the EGDS is well dispersed (usually after about 5 to 20 minutes) optional preservative are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the ammonium laureth sulfate, lauryl sulfate and other ingredients including the silicone premix are added to the finishing tank with ample agitation to insure a homogeneous mixture. A sufficient amount of the silicone premix is added to provide the desired level of dimethicone in the final product. Polyethylene glycol and optional Polyquaternium 10 are dispersed in water as a 1% to 10% solution before addition to the final mix. Once all ingredients have been added, ammonium xylene sulfonate or additional sodium chloride can be added to the mixture to thin or thicken respectively to achieve a desired product viscosity. Preferred viscosities range from about 3500 to about 9000 centistokes at 25° C. (as measured by a Wells-Brookfield cone and plate viscometer at 2/s at 3 minutes).

The compositions illustrated in Examples 10–14, all of which are embodiments of the present invention, provide excellent cleansing and conditioning of hair.

| | Example Number | | | | |
| --- | --- | --- | --- | --- | --- |
| Component | 10 | 11 | 12 | 13 | 14 |
| Ammonium laureth-2 sulfate | 5 | 3 | 2 | 10 | 8 |
| Ammonium lauryl sulfate | 5 | 5 | 4 | 5 | 8 |
| $MBAE_2S_{15}$ | 0.6 | 1 | 4 | 5 | 7 |
| Cocamide MEA | 0 | 0.68 | 0.68 | 0.8 | 0 |
| PEG 14M | 0.1 | 0.35 | 0.5 | 0.1 | 0 |
| Cocoamidopropylbetaine | 2.5 | 2.5 | 0 | 0 | 1.5 |
| Cetylalcohol | 0.42 | 0.42 | 0.42 | 0.5 | 0.5 |
| Stearylalcohol | 0.18 | 0.18 | 0.18 | 0.2 | 0.18 |
| Ethylene glycol distearate | 1.5 | 1.5 | 1.5 | 1.5 | 1.5 |
| Dimethicone[1] | 1.75 | 1.75 | 1.75 | 1.75 | 2.0 |
| Perfume solution | 0.45 | 0.45 | 0.45 | 0.45 | 0.45 |

-continued

| Component | Example Number | | | | |
|---|---|---|---|---|---|
| | 10 | 11 | 12 | 13 | 14 |
| DMDM hydantoin | 0.37 | 0.37 | 0.37 | 0.37 | 0.37 |
| Color solution (ppm) | 64 | 64 | 64 | 64 | 64 |
| Water and minors | - - - q. s. to 100% - - - | | | | |

[1]. Dimethicone is a 40 (gum)/60 (fluid) weight ratio blend of SE-76 dimethicone gum available from General Electric Silicones Division and a dimethicone fluid having a viscosity of 350 centistokes.

What is claimed is:

1. Liquid cleaning compositions comprising:
   a) as part of the surfactant system, from about 0.1% to about 50% by weight of a mid-chain branched surfactant substantially free from geminally-substituted branching selected from the group consisting of surfactants having the formula:

$$CH_3CH_2CH_2CH_2CH_2CH_2(CH_2)_{1-7}CH_2CH_2CH_2CH_2CH_2\text{---}B$$
   (Branching Range)

wherein:
   (i) one or more $C_1$–$C_3$ alkyl moieties branch from the longest linear carbon chain at one or more positions encompassed by the indicated branching range; and
   (ii) B is a hydrophilic moiety selected from sulfates and alkoxylated sulfates;
   b) as the other part of the surfactant system, from about 0.1% to about 50% by weight of one or more co-surfactants;
   c) from about 1% to about 99.7% by weight of solvent; and
   d) from about 0.1% to about 75% by weight of liquid cleaning composition adjunct ingredients.

2. The liquid cleaning composition according to claim 1 wherein the surfactant system comprises the mid-chain branched surfactant at levels of from about 1% to about 40% by weight of the surfactant system.

3. The liquid cleaning composition according to claim 1 wherein the surfactant system comprises the mid-chain branched surfactant:

$$\left[ CH_3CH_2(CH_2)_w\overset{R}{\underset{|}{C}}H(CH_2)_x\overset{R^1}{\underset{|}{C}}H(CH_2)_y\overset{R^2}{\underset{|}{C}}H(CH_2)_z \right]$$

wherein the total number of carbon atoms in the branched primary alkyl moiety of this formula, including the branching, is from 13 to 19.

4. The liquid cleaning composition according to claim 1 wherein the surfactant system comprises two or more of said mid-chain branched primary alkyl sulfates:

$$\left[ CH_3CH_2(CH_2)_w\overset{R}{\underset{|}{C}}H(CH_2)_x\overset{R^1}{\underset{|}{C}}H(CH_2)_y\overset{R^2}{\underset{|}{C}}H(CH_2)_zOSO_3M \right]$$

wherein the total number of carbon atoms in the branched primary alkyl moiety, including the branching, is from 14 to 20, and wherein further for this surfactant mixture the average total number of carbon atoms in the branched primary alkyl moieties having the above formula is within the range of greater than 14.5 to about 17.5.

5. The liquid cleaning composition according to claim 1 wherein the surfactant system comprises one or more $$\left[ CH_3CH_2(CH_2)_w\overset{R}{\underset{|}{C}}H(CH_2)_x\overset{R^1}{\underset{|}{C}}H(CH_2)_y\overset{R^2}{\underset{|}{C}}H(CH_2)_z(EO/PO)_mOSO_3\ M \right]$$

of said mid-chain branched primary alkyl alkoxylated sulfates wherein the total number of carbon atoms in the branched primary alkyl moiety, including the branching, but not including the carbon atoms in the alkoxy moiety, is from 14 to 20, and wherein further for this surfactant mixture the average total number of carbon atoms in the branched primary allkyl moieties having the above formula is within the range of greater than 14.5 to about 17.5; and the alkoxy moieties are selected from ethoxy, propoxy, and mixed ethoxy/propoxy groups.

6. The liquid detergent composition according claim 1 wherein the co-surfactant is selected from the group consisting of anionic surfactants, cationic surfactants, nonionic surfactants, amphoteric surfactants, and zwiterionic surfactants.

7. The liquid detergent compositions according to claim 1 wherein the co-surfactant comprises anionic surfactants selected from the group consisting of alkyl alkoxylated sulfates, alkyl sulfates, linear alkyl benzenesulfonates, and mixtures thereof.

8. The liquid detergent composition according to claim 1 comprising a builder.

9. The liquid detergent composition according to claim 1 comprising a detersive enzyme selected from the group consisting of proteases, lipases, cellulases, amylases, and mixtures thereof.

10. A liquid dishwashing composition according to claim 1.

11. A hair shampoo composition comprising:
   a) as part of the surfactant system, from about 0.1% to about 50% by weight of a mid-chain branched surfactant substantially free from geminally-substituted branching selected from the group consisting of surfactants having the formula:

$$CH_3CH_2CH_2CH_2CH_2CH_2(CH_2)_{1-7}CH_2CH_2CH_2CH_2CH_2\text{---}B$$
   (Branching Range)

wherein:
   (i) one or more $C_1$–$C_3$ alkyl moieties branch from the longest linear carbon chain at one or more positions encompassed by the indicated branching range; and
   (ii) B is a hydrophilic moiety selected from sulfates and alkoxylated sulfates;
   b) as the other part of the surfactant system, from about 0.1% to about 50% by weight of one or more co-surfactants;
   c) from about 1% to about 99.7% by weight of solvent; and
   d) from about 0.05% to about 10% by weight of one or more silicone hair conditioning agents; and e) from about 0.1% to about 75% by weight of shampoo composition adjunct ingredients.

12. The hair shampoo composition according claim 11 wherein the surfactant system comprises the mid-chain branched surfactant at levels of from about 0.1% to about 50% by weight of the surfactant system.

13. The shampoo composition according to claim 11 wherein the surfactant system comprises the mid-chain branched surfactant

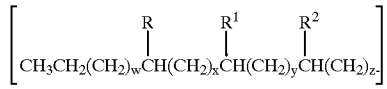

wherein the total number of carbon atoms in the branched primary alkyl moiety, including the branching, is from 13 to 19.

14. The shampoo composition according to claim 11 wherein the surfactant system comprises two or more of said mid-chain branched primary alkyl sulfates:

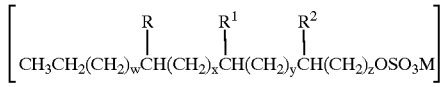

wherein the total number of carbon atoms in the branched primary alkyl moiety, including the branching, is from 14 to 20, and wherein the average total number of carbon atoms in the branched primary alkyl moieties is within the range of greater than 14.5 to about 17.5.

15. The shampoo composition according to claim 11 wherein the surfactant system comprises a mixture of two or more, of said mid-chain branched primary alkyl alkoxylated sulfates

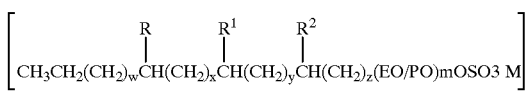

wherein the total number of carbon atoms in the branched primary alkyl moiety, including the branching, but not including the carbon atoms in the alkoxy moiety, is from 14 to 20, and wherein further for this surfactant mixture the average total number of carbon atoms in the branched primary alkyl moieties is within the range of greater than 14.5 to about 17.5; and the alkoxy moieties are selected from ethoxy, propoxy, and mixed ethoxy/propoxy groups.

16. The shampoo composition according to claim 11 wherein the co-surfactant is selected from the group consisting of anionic surfactants, cationic surfactants, nonionic surfactants, amphoteric surfactants, and zwiterionic surfactants.

17. The shampoo composition according to claim 11 wherein the co-surfactant comprises anionic surfactants selected from the group consisting of alkyl alkoxylated sulfates, alkyl sulfates, linear alkyl benzenesulfonates, and mixtures thereof.

18. The shampoo composition according to claim 11 comprising a builder.

19. The shampoo composition according to claim 11 wherein the co-surfactant comprises an anionic surfactant.

20. The shampoo composition according to claim 11 further comprising n antidandruff agent.

* * * * *